US008119588B2

(12) United States Patent
Bernhardt et al.

(10) Patent No.: US 8,119,588 B2
(45) Date of Patent: *Feb. 21, 2012

(54) HARD SURFACE CLEANER COMPOSITIONS OF SULFONATED ESTOLIDES AND OTHER DERIVATIVES OF FATTY ACIDS AND USES THEREOF

(75) Inventors: Randal J. Bernhardt, Antioch, IL (US); Lourdes R. Alonso, Deerfield, IL (US); Gregory P. Dado, Chicago, IL (US); Jacqueline Maas Pytel, Libertyville, IL (US)

(73) Assignee: Stepan Company, Northfield, IL (US)

( * ) Notice: Subject to any disclaimer, the term of this patent is extended or adjusted under 35 U.S.C. 154(b) by 234 days.

This patent is subject to a terminal disclaimer.

(21) Appl. No.: 12/507,786

(22) Filed: Jul. 22, 2009

(65) Prior Publication Data

US 2010/0184855 A1     Jul. 22, 2010

Related U.S. Application Data

(63) Continuation-in-part of application No. PCT/US09/031608, filed on Jan. 21, 2009.

(51) Int. Cl.
*C11D 1/28* (2006.01)
(52) U.S. Cl. .................................................. 510/495
(58) Field of Classification Search .................. 510/495
See application file for complete search history.

(56) References Cited

U.S. PATENT DOCUMENTS

| | | | |
|---|---|---|---|
| 2,581,375 A | 1/1952 | De Groote et al. |
| 2,743,288 A | 4/1956 | Rueggeberg et al. |
| 2,995,524 A | 8/1961 | Wylie et al. |
| 3,332,880 A | 7/1967 | Kessler et al. |
| 3,377,290 A | 4/1968 | Werner et al. |
| 3,664,961 A | 5/1972 | Norris |
| 3,668,153 A | 6/1972 | Crotty |
| 3,898,187 A | 8/1975 | Miller |
| 3,929,678 A | 12/1975 | Laughlin et al. |
| 4,228,044 A | 10/1980 | Cambre |
| 4,435,307 A | 3/1984 | Barbesgaard et al. |
| 4,438,025 A | 3/1984 | Satsuki et al. |
| 4,507,219 A | 3/1985 | Hughes |
| 4,548,744 A | 10/1985 | Connor |
| 4,561,998 A | 12/1985 | Wertz et al. |
| 4,597,898 A | 7/1986 | Vander Meer |
| 4,663,071 A | 5/1987 | Bush et al. |
| 4,816,188 A | 3/1989 | Kitano et al. |
| 4,936,551 A | 6/1990 | Behler et al. |
| 5,002,683 A | 3/1991 | Behler et al. |
| 5,071,594 A | 12/1991 | Borland et al. |
| 5,075,501 A | 12/1991 | Borland et al. |
| 5,294,726 A | 3/1994 | Behler et al. |
| 5,329,030 A | 7/1994 | Schenker et al. |
| 5,429,684 A | 7/1995 | Osberghaus et al. |
| 5,441,156 A | 8/1995 | Fabry et al. |
| 5,466,394 A | 11/1995 | de Buzzaccarini et al. |
| 5,576,282 A | 11/1996 | Miracle et al. |
| 5,622,925 A | 4/1997 | de Buzzaccarini et al. |
| 5,679,630 A | 10/1997 | Baeck et al. |
| 5,776,872 A | 7/1998 | Giret et al. |
| 5,883,062 A | 3/1999 | Addison et al. |
| 5,906,973 A | 5/1999 | Ouzounis et al. |
| 5,929,022 A | 7/1999 | Velazquez |
| 6,017,871 A | 1/2000 | Baeck et al. |
| 6,018,063 A | 1/2000 | Isbell |
| 6,048,836 A | 4/2000 | Romano et al. |
| 6,172,026 B1 | 1/2001 | Ospinal |
| 6,242,406 B1 | 6/2001 | Katsuda et al. |
| 6,294,513 B1 | 9/2001 | Jensen et al. |
| 6,306,812 B1 | 10/2001 | Perkins et al. |
| 6,326,348 B1 | 12/2001 | Vinson et al. |
| 6,605,579 B1 | 8/2003 | Arvanitidou et al. |
| 6,627,592 B1 | 9/2003 | Shamayeli |
| 6,797,011 B2 | 9/2004 | Blangiforti |
| 6,878,695 B2 | 4/2005 | Woo et al. |
| 6,903,064 B1 | 6/2005 | Kasturi et al. |
| 6,949,498 B2 | 9/2005 | Murphy et al. |
| 6,953,849 B2 | 10/2005 | Vali |
| 7,326,675 B2 | 2/2008 | Schneiderman et al. |
| 7,666,828 B2 | 2/2010 | Bernhardt et al. |
| 2002/0039979 A1 | 4/2002 | Aszman et al. |
| 2002/0187909 A1 | 12/2002 | Gupta et al. |
| 2004/0071653 A1 | 4/2004 | Bratescu et al. |
| 2004/0242920 A1 | 12/2004 | Dado et al. |
| 2005/0215456 A1 | 9/2005 | Goo et al. |
| 2007/0128129 A1 | 6/2007 | Stehr |
| 2007/0202069 A1 | 8/2007 | Tamareselvy |
| 2008/0015135 A1 | 1/2008 | Debuzzaccarini |
| 2009/0054294 A1 | 2/2009 | Theiler |

FOREIGN PATENT DOCUMENTS

| | | |
|---|---|---|
| DE | 2247832 | 4/1973 |
| DE | 3926345 A1 | 2/1991 |
| EP | 0070077 | 1/1983 |
| EP | 0075996 | 4/1983 |
| EP | 0094118 | 11/1983 |
| EP | 111965 | 6/1984 |
| EP | 111984 | 6/1984 |
| EP | 112592 | 7/1984 |

(Continued)

OTHER PUBLICATIONS

European Search Report in EP 09009490.5, dated May 17, 2010.
International Search Report and Written Opinion in PCT/US09/51312, dated Mar. 24, 2010.
International Search Report and Written Opinion in PCT/US10/29654, dated May 25, 2010.
Office Action in U.S. Appl. No. 12/506,861, dated Apr. 21, 2010.
Office Action in U.S. Appl. No. 12/506,861, dated Aug. 19, 2010.
Office Action in U.S. Appl. No. 12/506,977, dated Aug. 18, 2010.
A.J. Stirton, et al.: "Surface-active properties of salts of alpha-sulphonated acids and esters" Journal of the American Oil Chemists' Society, vol. 13, No. 1, Jan. 1954, pp. 13-16, XP002537683 Springer, Berlin, DE ISSN: 0003-021X DOI: 10.1007/BF02544763 The Whole Document.

(Continued)

*Primary Examiner* — John Hardee
(74) *Attorney, Agent, or Firm* — McAndrews, Held & Malloy, Ltd.

(57) ABSTRACT

Sulfo-estolides and formulations of sulfo-estolides in and as hard surface cleaners, glass cleaners, toilet bowl cleaners, carpet cleaners, all purpose cleaners, floor cleaners, and others are described. Further details of cleaning performance, stability of diluted and concentrated forms and contemplated cleaning applications are provided.

52 Claims, No Drawings

FOREIGN PATENT DOCUMENTS

| | | |
|---|---|---|
| EP | 0485500 A1 | 5/1992 |
| EP | 0 511 091 A1 | 10/1992 |
| GB | 1 047 772 A | 11/1966 |
| GB | 1082179 | 9/1967 |
| GB | 1278421 A1 | 6/1972 |
| GB | 1372034 | 10/1974 |
| GB | 1 380 390 A | 1/1975 |
| GB | 2075028 | 11/1981 |
| GB | 2095275 | 9/1982 |
| GB | 2247832 | 3/1992 |
| WO | 88/09367 | 12/1988 |
| WO | 89/09813 | 10/1989 |
| WO | WO 90/02116 A1 | 3/1990 |
| WO | WO 91/02045 A1 | 2/1991 |
| WO | WO 91/13961 A1 | 9/1991 |
| WO | 92/05249 | 4/1992 |
| WO | WO 92/15660 A1 | 9/1992 |
| WO | 99/05242 | 2/1999 |
| WO | 00/18363 A1 | 4/2000 |
| WO | 00/58430 A1 | 10/2000 |
| WO | 01/53247 A1 | 7/2001 |
| WO | 2005/113735 A1 | 12/2005 |
| WO | 2006/062665 | 6/2006 |
| WO | 2008/137769 | 11/2008 |
| WO | 2009/094336 | 7/2009 |

OTHER PUBLICATIONS

PCT International Search Report and Written Opinion from International Application No. PCT/US2009/031455 mailed on Aug. 17, 2009.

PCT International Search Report and Written Opinion from International Application No. PCT/US2009/031608 mailed on Oct. 29, 2009.

PCT International Search Report and Written Opinion from International Application No. PCT/US2009/051299 mailed on Oct. 20, 2009.

PCT International Search Report and Written Opinion from International Application No. PCT/US2009/051318 mailed on Oct. 22, 2009.

PCT International Search Report and Written Opinion from International Application No. PCT/US2009/051319 mailed on Oct. 20, 2009.

PCT International Search Report and Written Opinion from International Application No. PCT/US2009/051464 mailed on Oct. 22, 2009.

Foams Fundamentals and Applications in the Petrochemical Industry, edited by Laurier L. Schraman (1994).

Handbook of Water-Soluble Gums and Resins, Glossary and Chapters 3, 4, 12 and 13, Robert L. Davidson, McGraw-Hill Book Co., New York, NY (1980).

Stein et al., J. Amer. Oil Chemists Soc., 52:323-329 (1975).

Knaggs et al., J. Amer. Oil Chemists Soc., 42(9):805-810 (1965).

Kato et al., J. Surfactants and Detergents, 6(4):331-337 (2003).

Kirk-Othmer, Encyclopedia of Chemical Technology, 5th ed., vol. 23, Wiley-Interscience, Hoboken, NJ (2007), "Sulfonation and Sulfation", pp. 513-562.

McCutcheons' 2009 Functional Materials of North American Edition, vol. 2, pp. 239-246 (2009).

Neiditch et al., J. Amer. Oil Chemists Soc., 57(12):426-429 (1980).

Office Action in U.S. Appl. No. 12/353,751, dated Dec. 1, 2009.

Office Action in U.S. Appl. No. 12/353,751, dated Nov. 17, 2009.

Office Action in U.S. Appl. No. 12/506,977, dated Apr. 16, 2010.

Steinberg, Preservatives for Cosmetics Manual, 2nd Ed., by David S. Steinbens (2006).

Sauls et al., J. Amer. Oil Chemists Soc., 33(9):383-389 (1956).

SDA "Washers and Detergents" publication 2005; http://www.cleaning101.com/laundry/HE.pdf.

Surfactants and Interfacial Phenomena, 3rd ed., by Milton Rosen, published by John Wiley & Sons, Inc., Hoboken, NJ (2004).

HARD SURFACE CLEANER COMPOSITIONS OF SULFONATED ESTOLIDES AND OTHER DERIVATIVES OF FATTY ACIDS AND USES THEREOF

RELATED APPLICATIONS

This application claims priority to international PCT Application Serial No. PCT/US09/31608 entitled, "SULFONATED ESTOLIDES AND OTHER DERIVATIVES OF FATTY ACIDS AND USES THEREOF" filed on Jan. 21, 2009, the complete matter of which is incorporated herein by reference in its entirety.

BACKGROUND OF THE INVENTION

The present technology, in general, relates to sulfo-estolides. More particularly, the present technology relates to compositions of sulfo-estolides derivatives and salts of sulfo-estolides and the various applications and/or processes of utilizing them as hard surface cleaners.

BRIEF SUMMARY OF THE INVENTION

The present technology generally relates to sulfonated estolide compositions comprising a sulfonated estolide and a carrier, as well as additional compositions containing one or more further components. For example, additional solvents, surfactants, buffers, biocidal agents, disinfecting agents, adjuvants, and/or other additives can be added to the sulfonated estolide and carrier-based composition to increase cleaning performance depending on, for example, the level of soiling and surface to be cleaned. The present technology has superior or equal cleaning performance when compared to other standard cleaning agents; the added benefit of particularly "green" or "eco-friendly" compositions; and the ability to be concentrated which further decreases any negative environmental impact. Compositions of the present technology, including the concentrated and non-concentrated "green" compositions, can also be stored before or after dilution and maintain stability for a prolonged period of time, which is another advantageous outcome of the present technology.

One aspect of the present technology is a biodegradable surfactant composition, comprising: about 0.1% to about 99.9% by weight of at least one surfactant having the following general Formula 1:

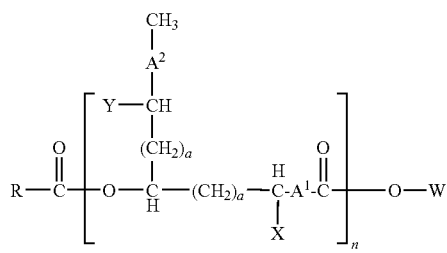

Formula 1 wherein n is an integer from 1-30, or mixtures thereof; one of X and Y is $SO_3$—Z, the other of X and Y is H, and X and Y are independently assigned in each repeating unit; $A^1$ and $A^2$ are linear or branched, saturated or unsaturated, substituted or un-substituted, alkyl diradicals wherein the total number of carbons for each repeating unit is independent and in the range of $C_8$ to $C_{22}$; a is 0, 1, or 2, and is independently assigned in each repeating unit; R is linear or branched, saturated or unsaturated, substituted or unsubstituted hydrocarbon wherein the total number of carbon atoms is from 1 to 24; W is H or a monovalent or divalent metal cation, ammonium cation, substituted ammonium cation, or an alkyl or substituted alkyl group; and Z is H or a monovalent or divalent metal cation, ammonium or substituted ammonium cation; and about 0.1% to about 99.9% of at least one carrier; wherein the composition is a hard surface or substrate cleaner; and wherein the composition is biodegradable.

Another aspect of the present technology is a method of cleaning at least one surface or substrate, comprising the steps of: providing a composition comprising about 0.1% to about 99.9% by weight of at least one surfactant having the following general Formula 1:

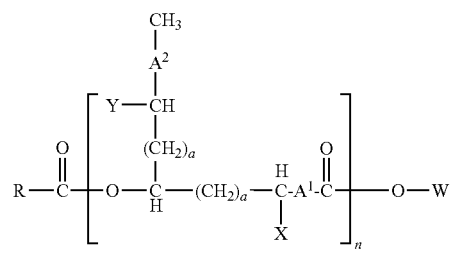

Formula 1 wherein n is an integer from 1-30, or mixtures thereof; one of X and Y is $SO_3$—Z, the other of X and Y is H, and X and Y are independently assigned in each repeating unit; $A^1$ and $A^2$ are linear or branched, saturated or unsaturated, substituted or un-substituted, alkyl diradicals wherein the total number of carbons for each repeating unit is independent and in the range of $C_8$ to $C_{22}$; a is 0, 1, or 2, and is independently assigned in each repeating unit; R is linear or branched, saturated or unsaturated, substituted or unsubstituted hydrocarbon wherein the total number of carbon atoms is from 1 to 24; W is H or a monovalent or divalent metal cation, ammonium cation, substituted ammonium cation, or an alkyl or substituted alkyl group; and Z is H or a monovalent or divalent metal cation, ammonium or substituted ammonium cation; and about 0.1% to about 99.9% of at least one carrier; contacting at least one soiled surface or substrate with the composition; and removing the composition and soil from the surface or substrate.

A further embodiment of the present technology is an all-purpose general cleaning composition, comprising: about 0.1% to about 99.9% by weight of at least one surfactant having the following general Formula 1:

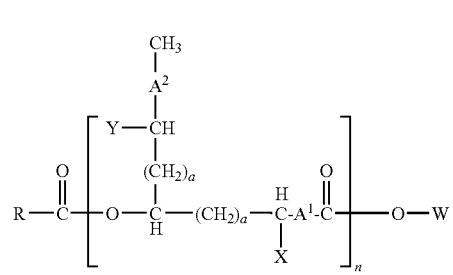

Formula 1 wherein n is an integer from 1-30, or mixtures thereof; one of X and Y is $SO_3$—Z, the other of X and Y is H, and X and Y are independently assigned in each repeating unit; $A^1$ and $A^2$ are linear or branched, saturated or unsaturated, substituted or un-substituted, alkyl diradicals wherein the total number of carbons for each repeating unit is independent and in the range of $C_8$ to $C_{22}$; a is 0, 1, or 2, and is independently assigned in each repeating unit; R is linear or branched, saturated or unsaturated, substituted or unsubstituted hydrocarbon wherein the total number of carbon atoms is from 1 to 24; W is H or a monovalent or divalent metal cation, ammonium cation, substituted ammonium cation, or an alkyl or substituted alkyl group; and Z is H or a monovalent or divalent metal cation, ammonium or substituted ammonium cation; about 1% to about 10% of at least one nonionic surfactant; about 0.1% to about 10% of at least one adjuvant/builder; about 0.1% to about 10% of at least one buffer; about 0.5% to about 50% of at least one solvent; about 0.1% to about 2% of at least one additive; optionally about 0.1% to about 5% of at least one disinfecting agent; optionally about 0.1% to about 10% of at least one anionic surfactant; and about 0.1% to about 99.9% of at least one carrier.

Still a further embodiment of the present invention is a glass cleaning composition, comprising: about 0.1% to about 99.9% by weight of at least one surfactant having the following general Formula 1:

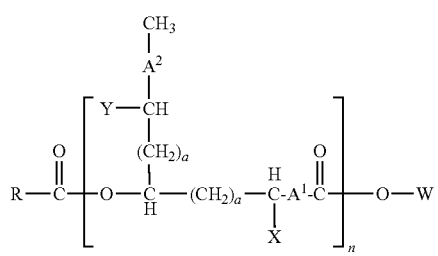

Formula 1 wherein n is an integer from 1-30, or mixtures thereof; one of X and Y is $SO_3$—Z, the other of X and Y is H, and X and Y are independently assigned in each repeating unit; $A^1$ and $A^2$ are linear or branched, saturated or unsaturated, substituted or un-substituted, alkyl diradicals wherein the total number of carbons for each repeating unit is independent and in the range of $C_8$ to $C_{22}$; a is 0, 1, or 2, and is independently assigned in each repeating unit; R is linear or branched, saturated or unsaturated, substituted or unsubstituted hydrocarbon wherein the total number of carbon atoms is from 1 to 24; W is H or a monovalent or divalent metal cation, ammonium cation, substituted ammonium cation, or an alkyl or substituted alkyl group; and Z is H or a monovalent or divalent metal cation, ammonium or substituted ammonium cation; about 1% to about 3% of at least one nonionic surfactant; about 0.5% to about 40% of at least one solvent; optionally about 0.1% to about 5% of at least one buffer; optionally about 0.1% to about 2% of at least one adjuvant/builder; optionally about 0.1% to about 10% of at least one amphoteric surfactant; optionally about 0.1% to about 1% of at least one anionic surfactant; and about 0.1% to about 99.9% of at least one carrier.

Another embodiment of the present technology is an bathroom cleaning composition, comprising: about 0.1% to about 99.9% by weight of at least one surfactant having the following general Formula 1:

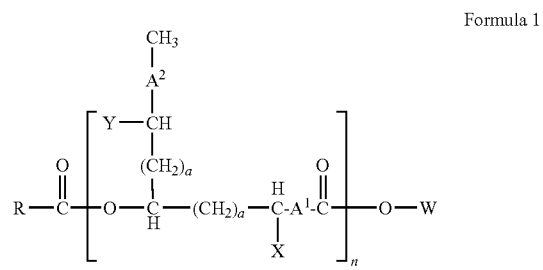

Formula 1 wherein n is an integer from 1-30, or mixtures thereof; one of X and Y is $SO_3$—Z, the other of X and Y is H, and X and Y are independently assigned in each repeating unit; $A^1$ and $A^2$ are linear or branched, saturated or unsaturated, substituted or un-substituted, alkyl diradicals wherein the total number of carbons for each repeating unit is independent and in the range of $C_8$ to $C_{22}$; a is 0, 1, or 2, and is independently assigned in each repeating unit; R is linear or branched, saturated or unsaturated, substituted or unsubstituted hydrocarbon wherein the total number of carbon atoms is from 1 to 24; W is H or a monovalent or divalent metal cation, ammonium cation, substituted ammonium cation, or an alkyl or substituted alkyl group; and Z is H or a monovalent or divalent metal cation, ammonium or substituted ammonium cation; optionally about 0.1% to about 5% of at least one nonionic surfactant; optionally about 0.5% to about 10% of at least one solvent; optionally about 0.1% to about 10% of at least one buffer; optionally about 0.1% to about 15% of at least one additive; optionally about 0.1% to about 15% of at least one disinfecting agent; optionally about 0.1% to about 2% of at least one adjuvant/builder; optionally about 0.1% to about 2% of at least one amphoteric surfactant; optionally about 0.1% to about 6% of at least one anionic surfactant; and about 0.1% to about 99.9% of at least one carrier.

Still a further embodiment of the present technology is a floor cleaning composition, comprising: about 0.1% to about 99.9% by weight of at least one surfactant having the following general Formula 1:

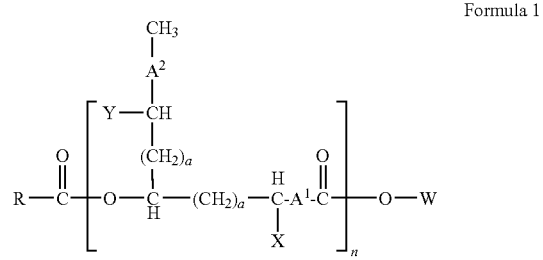

Formula 1 wherein n is an integer from 1-30, or mixtures thereof; one of X and Y is $SO_3$—Z, the other of X and Y is H, and X and Y are independently assigned in each repeating unit; $A^1$ and $A^2$ are linear or branched, saturated or unsaturated, substituted or un-substituted, alkyl diradicals wherein the total number of carbons for each repeating unit is independent and in the range of $C_8$ to $C_{22}$; a is 0, 1, or 2, and is independently assigned in each repeating unit; R is linear or branched, saturated or unsaturated, substituted or unsubstituted hydrocarbon wherein the total number of carbon atoms is from 1 to 24; W is H or a monovalent or divalent metal cation, ammonium cation, substituted ammonium cation, or an alkyl or substituted alkyl group; and Z is H or a monovalent or divalent metal cation, ammonium or substituted ammonium cation; optionally about 0.1% to about 14% of at least one nonionic surfactant; optionally about 0.5% to about 30% of at least one solvent; optionally about 0.1% to about 2% of at least one buffer; optionally about 0.1% to about 5% of at least one disinfecting agent; optionally about 0.1% to about 5% of at least one biocidal agent; optionally about 0.1% to about 10% of at least one amphoteric surfactant; optionally about 0.1% to about 10% of at least one anionic surfactant; about 0.1% to about 2% of at least one additive; and about 0.1% to about 99.9% of at least one carrier.

Yet a further embodiment of the present technology is a biocidal composition, comprising: about 0.1% to about 99.9% by weight of at least one surfactant having the following general Formula 1:

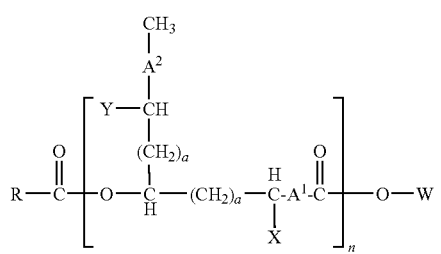

Formula 1 wherein n is an integer from 1-30, or mixtures thereof; one of X and Y is $SO_3$—Z, the other of X and Y is H, and X and Y are independently assigned in each repeating unit; $A^1$ and $A^2$ are linear or branched, saturated or unsaturated, substituted or un-substituted, alkyl diradicals wherein the total number of carbons for each repeating unit is independent and in the range of $C_8$ to $C_{22}$; a is 0, 1, or 2, and is independently assigned in each repeating unit; R is linear or branched, saturated or unsaturated, substituted or unsubstituted hydrocarbon wherein the total number of carbon atoms is from 1 to 24; W is H or a monovalent or divalent metal cation, ammonium cation, substituted ammonium cation, or an alkyl or substituted alkyl group; and Z is H or a monovalent or divalent metal cation, ammonium or substituted ammonium cation; about 0.001% to about 40% by weight of at least one biocidal agent; and about 0.1% to about 99.99% of at least one carrier.

DETAILED DESCRIPTION OF THE INVENTION

The present technology, in general, relates to sulfo-estolides. More particularly, the present technology relates to compositions of sulfo-estolides derivatives and salts of sulfo-estolides and the various applications and/or processes of utilizing them as hard surface cleaners, for example. The compositions described here include, but are not limited to, sulfo-estolides having the structure following general Formula 1:

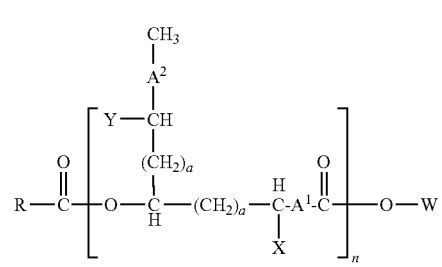

Formula 1

In Formula 1:
n is an integer from about 1 to about 30, alternatively about 1 to about 10, alternatively 1 to 4, alternatively 1, 2, or 3, alternatively 1 or 2, alternatively 1; or mixtures thereof;
One of X and Y is $SO_3^-Z$, the other of X and Y is H (i.e., hydrogen), and X and Y are independently assigned in each repeating unit;
$A^1$ and $A^2$ are independently selected linear or branched, saturated or unsaturated, substituted or unsubstituted alkyl diradicals, where the total number of carbons for each repeating unit is independent and in the range of $C_8$ to $C_{22}$. As defined here, the term "alkyl diradical" is meant to refer to a linking hydrocarbon or alkylene segment, for example, but by no means limited to —$(CH_2)_3$—, —$(CH_2)_4$—, —$(CH_2)_5$—, and so forth;
a is 0, 1, or 2, and is independently assigned in each repeating unit. When a=0, 1, or 2, the functional group corresponds to an alpha-sulfo-estolide, beta-sulfo-estolide, or gamma-sulfo-estolide, respectively;
R can be linear or branched, saturated or unsaturated, substituted or unsubstituted hydrocarbon, wherein the total number of carbon atoms can be from 1 to about 24. In at least one embodiment, R has from about 7 to about 21 carbon atoms, alternatively from about 8 to about 16 carbon atoms, and can be a saturated or unsaturated linear or branched hydrocarbon, a linear or branched hydroxyalkane sulfonate, or a linear or branched alkene sulfonate. For example, in one embodiment, $A^1$ and $A^2$ are linear alkyl diradicals and R is saturated or unsaturated linear hydrocarbon, linear hydroxyalkane sulfonate, or linear alkene sulfonate having from about 7 to about 21 carbon atoms, alternatively from about 8 to about 16 carbons;
W is a monovalent or divalent metal; ammonium; substituted ammonium; H (i.e., hydrogen); or a linear or branched, substituted or unsubstituted alkyl having from 1 to about 22 carbon atoms. For example, W can be an alkali or alkaline earth metal cation. Alternatively, W can be a glycerine joined by an ester linkage, e.g., a substituted C3 alkyl such that the structure of general Formula 1 is incorporated one or more times as an ester in a monoglyceride, a diglyceride, or a triglyceride; and
Z is H (i.e., hydrogen) or a monovalent or divalent metal cation, ammonium or substituted ammonium cation, preferably an alkali or alkaline earth metal cation, for example potassium, sodium, calcium, or magnesium, with potassium being preferred in certain embodiments.

The above structure is illustrative of the sulfo-estolide products that may be derived from, for example, linear unsaturated fatty acid feedstocks. It is understood and will be appreciated by at least those skilled in the art that sultone hydrolyzed products and structures of a comparable nature may be derived from branched and/or substituted unsaturated fatty acids or mixtures of linear and branched and/or substituted unsaturated fatty acids.

Additional sulfo-estolide compositions of the present technology may be produced from fatty acid feedstocks comprising polyunsaturated fatty acids, where $A^1$ and $A^2$ may be independently selected from the set of alkyl diradicals that are, for example, a) saturated; b) unsaturated; c) unsaturated and substituted with a sulfonate group; d) substituted with a hydroxyl group and a sulfonate group; or e) substituted with a ester group and a sulfonate group (i.e., a sulfo-estolide).

In another embodiment of the present technology, the sulfo-estolide compositions are comprised of carboxylic esters, or are reported in an ester analysis as carboxylic esters. Although it is contemplated that at least some of these carboxylic esters are sulfo-estolides, the presently described technology is not limited by the accuracy of this belief, for example, the compositions may contain carboxylic esters wherein X and Y within one or more repeating units, in general Formula 1, are both H (i.e., hydrogen).

In an additional aspect, the present technology provides a process of making a sulfo-estolide mixture comprising the steps of providing at least one unsaturated fatty carboxylic acid having from about 8 to about 24 carbon atoms; providing at least one chain termination agent having from about 4 to about 24 carbon atoms; sulfonating the unsaturated fatty carboxylic acid to form a sulfonated intermediate; and reacting the chain termination agent with the sulfonated intermediate to form a sulfo-estolide mixture.

In another embodiment of the present technology, the sulfo-estolide compositions are comprised of sulfo-estolide of the general Formula 1 and a non-sulfonated estolide which comprises two or more fatty acid chains that does not contain a sulfonate group.

Definitions

The term "sulfo-estolide" ("SE") is used herein to describe general Formula 1. The term "partially hydrolyzed sulfo-estolide" ("PHSE") describes compositions of general Formula 1 wherein the esters have been partially hydrolyzed between (about 1% to about 95%). The term "hydrolyzed sulfo-estolide" ("HSE") describes compositions of general Formula 1 wherein the esters have been fully hydrolyzed (greater than about 95%, for example).

The term "sultone hydrolyzed product" ("SHP") is used here to describe salts of sulfo-estolides that are produced from feedstock comprising unsaturated fatty acids by a process comprising the steps of sulfonation with $SO_3$, neutralization, and hydrolysis of sultones. The neutralization and hydrolysis are conducted at a level of caustic addition that maintains the pH in the range from about 4 to about 10.

The resulting product of neutralization and hydrolysis contains carboxylic acid esters at a level that corresponds to about 5 to about 95 mol %, alternatively about 20 mol % to about 60 mol %, alternatively about 20 mol % to about 45 mol %, alternatively about 30 mol % to about 45 mol % of the total carboxylic functionality in the composition. Although not wanting to be bound by any particular theory, it is believed that none or few of the esters (whether they are sulfo-estolides or not) are hydrolyzed in the process of making SHP. By processing at a low temperature and neutralizing the acid as it leaves the sulfonator as quickly as possible, it is further believed that lower ester levels will be obtained. Through improved and/or enhanced process conditions for production of esters, it is contemplated that products that have higher ester content will be obtained. For example, it is also believed that the ester content may be obtained at lower and/or higher levels through the selection of the molar ratio of $SO_3$ to alkene functionality used in the sulfonation step, or alternatively or in addition, through the selection of the amount of monounsaturated and/or polyunsaturated fatty acids comprising the unsaturated fatty acid feedstock.

The term "ester hydrolyzed product" ("EHP") is used herein to describe a sulfonate composition that is produced from unsaturated fatty acids by sulfonation with $SO_3$ to produce sulfo-estolide and subsequent hydrolysis of greater than about 95% of the carboxylic esters. For example the resulting product may have a carboxylic ester content that corresponds to less than about 5 mol %, alternatively less than about 2 mol %, alternatively less than about 1 mol % of the total carboxylic functionality in the composition.

The term "partially ester hydrolyzed products" ("PEHP") is used herein to describe salts of sulfo-estolides that are produced from unsaturated fatty acids by sulfonation with $SO_3$ and hydrolysis of a portion of the carboxylic esters. The molar percentage of hydrolysis of carboxylic esters that is realized is from about 1% to about 95%, alternatively from about 5% to about 90%, alternatively from about 10% to about 90%, alternatively from about 20% to about 90%.

A "repeating unit" means one instance of the subject matter enclosed by brackets in a formula. For example, if n=15 for a given molecule according to general Formula 1, the molecule has 15 instances of the bracketed structure. Each instance of the bracketed structure can be identical to or different from other instances of the bracketed structure. For example, the Y moiety in general Formula 1 can be H (i.e., hydrogen) in one repeating unit and $—SO_3^-Z$ in another repeating unit of the same molecule.

The term "hard surfaces" as used herein are, for example and in some cases preferable, hard-surfaces typically found in and around residential dwellings like bathrooms, kitchens, basements and garages, e.g., floors, walls, tiles, windows, sinks, showers, shower plasticized curtains, wash basins, drains, dishes, fixtures, and fittings and the like made of different materials like fiberglass and other car materials, leather, ceramic, painted and un-painted wood or concrete (for example, as a graffiti remover), varnished or sealed, plaster, bricks, vinyl, no-wax vinyl, linoleum, marble, melamine, Formica® (commercially available from Formica Corporation, located in Cincinnati, Ohio), Corian® (commercially available from DuPont, located in Wilmington, Del.), glass, any plastics, metals, chromed surfaces and the like. "Hard surfaces" also includes household appliances including, but not limited to, washing machines, automatic dryers, refrigerators, freezers, ovens, microwave ovens, dishwashers, etc. Still further, "hard surfaces" include those associated with medical facilities, e.g., hospitals, clinics as well as laboratories among other industrial and/or commercial settings including, but not limited to restaurants, full service and fast food, sports facilities and other facilities using janitorial staff, and those found in cleaning industrial parts such as automobile and airplane engines, metal parts, in removal of oils, greases and lubricants, attached thereto, on, in or the like.

However, it will also be appreciated and understood by those skilled in the art that compositions of the present technology can be used on or in connection with other surfaces, materials, or substrates, for example, industrial and commercial carpets, fabrics, non-wovens, industrial covers, and the like.

Making SE or Other Carboxylic Esters

At least one process of making sulfo-estolides mixtures of the present technology, includes the methods of hydrolyzing sultones, hydrolyzing carboxylic esters and steps of bleaching the sulfo-estolides of the present technology is described in PCT Application Serial No. PCT/US09/31608, the complete matter of which is incorporated herein by reference in its entirety.

A suitable starting material for the present process of making one or more components and/or formulations of the present technology, for example, is a fatty acid (fatty carboxylic acid). Fatty acids that may be suitable for use in the present technology include, but are not limited to, linear unsaturated fatty acids of about 8 to about 24 carbons, branched unsaturated fatty acids of about 8 to about 24 carbons, or mixtures thereof. Unsaturated fatty acids provided from commercial sources containing both saturated and unsaturated fatty acids are suitable for use in the practice of the present technology. Mixtures of saturated fatty acids and unsaturated fatty acids are also contemplated. In a non-limiting example, fatty acid mixtures that are rich in oleic acid (cis-9-octadecenoic acid) are suitable feedstocks. Other unsaturated fatty acids, for example but not limited to, trans-octadecenoic acids or palmitoleic acid may also be employed in the presently described technology.

Suitable feedstocks may be derived from vegetable and/or animal sources, including but not limited to fatty acids and fatty acid mixtures derived from, for example, canola oil, corn oil, cottonseed oil, linseed oil, olive oil, palm oil, peanut oil, rapeseed oil, safflower oil, sesame oil, soybean oil, sunflower oil, tall oil, tung oil, lard, poultry fat, BFT (bleachable fancy tallow), edible tallow, coconut oil, cuphea oil, yellow grease and combinations of these. Also contemplated are genetically modified or engineered oils that include, but are not limited to high oleic sunflower or soybean oil. In some embodiments, the preferred unsaturated fatty acid feedstock content may contain reduced levels of polyunsaturated fatty acids, for example, less than about 15%, alternatively less than about 10%, alternatively less than about 5% on a total weight basis. In some additional embodiments, the fatty acid feedstocks may be obtained by the partial hydrogenation of unsaturated triglycerides, for example, soybean oil followed by hydrolysis of the oil to afford fatty acids that are enriched in monounsaturated fatty acids and depleted in polyunsaturated fatty acids. The above-noted triglycerides optionally hydrogenated, can also be used as feedstocks, alone or in combination with fatty acids. Still further, in some embodiments of the presently described technology, suitable feedstocks may include those that contain appreciable amounts of saturated fatty acids, for example, up to about 80%, for example, alternatively up to about 50%, alternatively up to about 30%, alternatively up to about 20% saturated fatty acid by weight. Alternatively, the feedstocks may be enriched in mono-unsaturated fatty acids, for example, via distillation; however, undistilled feedstocks are preferred due to lower cost.

In certain embodiments, a chain termination agent can be included in the reaction to reduce or prevent the formulation of products of general Formula 1 in which n is greater than one. The chain termination agent can be, for example, a saturated or unsaturated, substituted or unsubstituted, aliphatic or aromatic carboxylic acid having from about 7 to about 22 carbon atoms, or a combination of any two or more of these. The contemplated characteristic of a chain termination agent preferred for the present purpose is that it can form an ester. One class of preferred chain termination agents is a saturated fatty acid having from about 8 to about 22 carbon atoms, optionally from about 8 to about 14 carbon atoms, optionally about 8, about 10, or about 12 carbon atoms or mixtures of these fatty acid species.

Product Descriptions

The compositions of the present technology utilizing the general Formula 1 are complex mixtures of compounds that are monomeric, dimeric, and higher-order oligomeric species in terms of the number of originating fatty acid chains. The oligomerization in these mixtures is via the formation of ester linkages. Branched oligomers are also present in some embodiments.

The sulfo-estolide functional group corresponds structurally to the condensation of the hydroxyl group of an internal hydroxy sulfonate of fatty acid with the carboxylic acid group of a second fatty acid chain, where the second fatty acid chain may be, but is not necessarily limited to: a) an unsaturated or saturated fatty acid; b) an internal hydroxy sulfonate of fatty acid; c) an internal alkene sulfonate or corresponding cyclic anhydride (i.e. sultone) of fatty acid; or d) an internal mono- or poly sulfo-estolide of two or more fatty acids (i.e., trimer, tetramer, etc.). The position of the sulfonate group along the back bone of the fatty acid chains is dictated by the location of the double bond in the starting material (9-octadecenoic acid for example) and the "direction" in which $SO_3$ adds across the double bond (thus, 9- and 10-sulfonate positions from oleic acid).

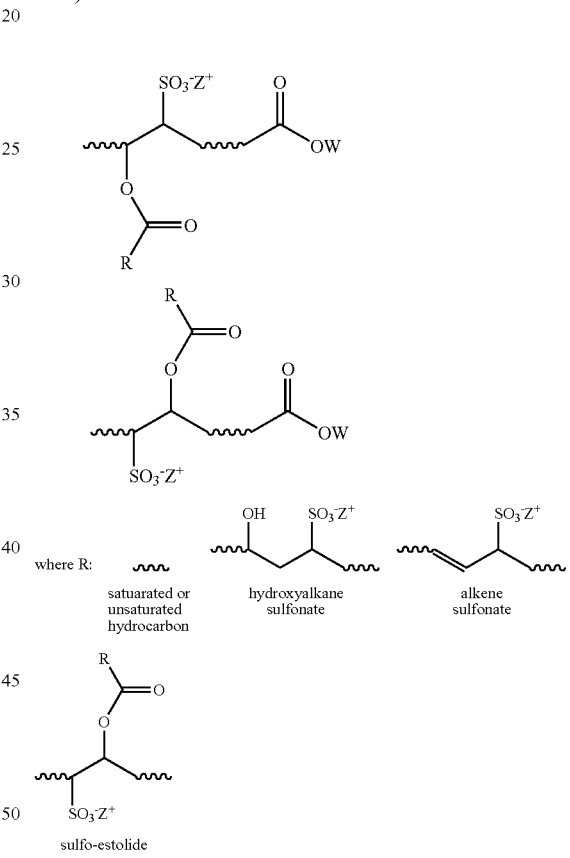

Non-ester-containing monomeric components made by this process are believed to comprise, in part, specific internal hydroxy sulfonates of fatty acid. For example, with 9-octadecenoic acid, the sulfonate groups are believed to be attached to the 9-position and alternatively the 10-position of the fatty acid. Examples are shown below.

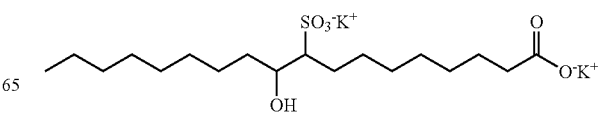

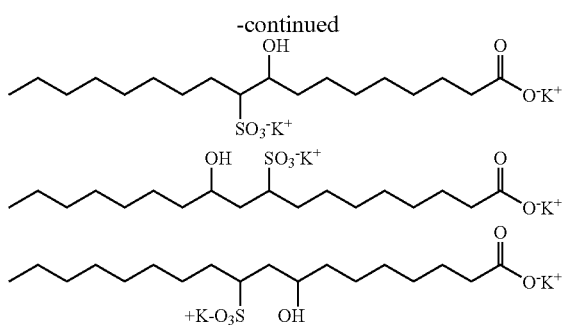

The monomeric components are further believed to comprise, in part, specific internal alkene sulfonates of fatty acid. These components may comprise cis- and/or trans-double bonds. It is also possible that compounds are present where the unsaturation is at the position of the sulfonate group (i.e., vinylic sulfonates). Examples are shown below.

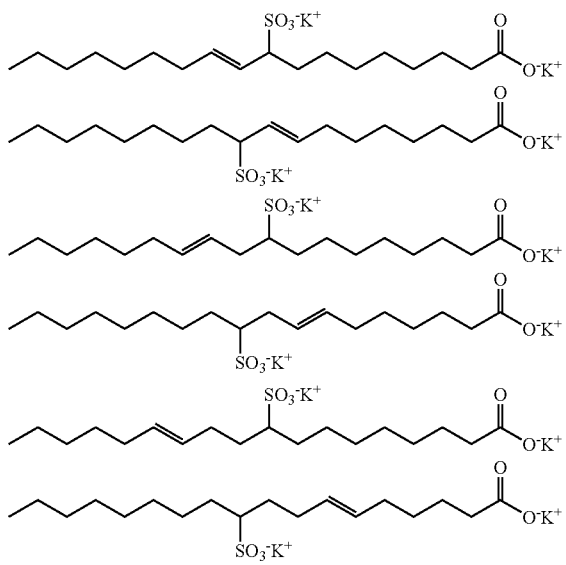

The monomeric components may further comprise disulfonated species, unsaturated fatty acids, and saturated fatty acids.

EHP is sometimes used herein as a designation for sulfonated products that have been subjected to complete hydrolysis of sulfo-estolide functionality. Such hydrolysis can be accomplished by, for example, treatment of SHP with excess base under high pH conditions (for example, a pH greater than about 11) at elevated temperatures (for example, about 85° C. to about 100° C.). EHP is believed to comprise a mixture of hydroxyalkane sulfonates and alkene sulfonates of comparable structure to the monomeric components of sulfo-estolide compositions, though not necessarily in comparable ratios. This mixture is comparable in composition to the compositions of sulfonated unsaturated fatty acids that are described in the art, for example, in T. W. Sauls and W. H. C. Rueggeberg, Journal of the American Oil Chemists Society (JAOCS), Volume 33, Number 9, September, 1956, pp 383-389.

It can be appreciated by at least those skilled in the art that PEHP will be comprised of elevated amounts of monomeric hydroxyalkane sulfonates and alkene sulfonates while maintaining some level of sulfo-estolide functionality.

Formulation Applications for SE

The formulations of the present technology utilizing general Formula 1 are suitable to clean, for example, hard surfaces, among other substrates. Any type of surface prone to soiling can be cleaned by one or more of the formulations or combinations thereof, herein described.

In a preferred embodiment, the surfaces set forth herein are hard surfaces composed of refractory materials such as: glazed and unglazed tile, porcelain, ceramics as well as stone including marble, granite, and other stones surfaces; glass; metals, e.g., stainless steel or aluminum; plastics e.g. polyester, vinyl; fiberglass, Formica® (commercially available from Formica Corporation, located in Cincinnati, Ohio), Corian® (commercially available from DuPont, located in Wilmington, Del.) and other hard surfaces known to the industry. Even more preferably, the hard surfaces herein are lavatory fixtures such as shower stalls, bathtubs and bathing appliances (racks, shower doors, shower bars) toilets, bidets, wall and flooring surfaces especially those which include refractory materials, among others. Even more preferably, the hard surface herein are those associated with kitchen environments and other environments associated with food preparation, including cabinets and countertop surfaces as well as walls and floor surfaces especially those which include refractory materials, plastics, Formica® (commercially available from Formica Corporation, located in Cincinnati, Ohio), Corian® (commercially available from DuPont, located in Wilmington, Del.) and stone. Hard surface cleaning products of the present technology can be made at a neutral pH, but often are made into formulations that exhibit an acid or alkaline pH to get improved cleaning. The stains and soils that are removed from hard surfaces can be organic or inorganic in nature. The type of soils that are to be removed may dictate the preferred pH of the resultant cleaning formula desired. When used as a neutral general purpose cleaner, the sulfonated estolide formulation should have a pH of about 6.0 to about 9.0. A neutral pH is preferred for safety of the user and for hard surface materials which can be adversely affected by high alkaline or acidic cleaners.

In another preferred embodiment, the sulfonated estolide formulation can be used as a degreaser in a heavy duty cleaning application, which could address, for example, engine grease and other lubricant deposits undesirable onto surfaces, such as hard surfaces. Degreaser formulations of the present technology can exhibit, for example, a pH ranging from about 5 to about 13. Sulfonated estolide surfactants for use in degreasing applications can be in the range of about 0.1% to about 80% weight of active ingredient, preferably about 0.1 to about 35% or about 0.1 to about 20% for concentrated formulations or about 0.1% to about 15% for ready-to-use formulations. Concentrates can also be formulated for degreasing applications. Although most preferably the degreasing formulation for household use will be commercially sold as a ready-to-use formulation, concentrated versions are also contemplated. Degreaser formulations for industrial and institutional use are preferably concentrated to about 5×, about 10×, or about 20×. Industrial and institutional degreasing formulations can also be sold as ready-to-use formulations.

In a further preferred embodiment, the sulfonated estolide formulation can be used in a toilet bowl cleaning application. Toilet bowl cleaner formulations of the present technology can exhibit, for example, a pH less than about 5. Sulfonated estolide surfactants for use in toilet bowl cleaning applications can be in the range of about 0.1% to about 80% weight of active ingredient, preferably about 0.1 to about 35% or about 0.1% to about 20% for concentrated formulations or about 0.1% to about 15% for ready-to-use toilet bowl cleaning formulations. Concentrates can also be formulated for toilet bowl cleaning applications. Although most preferably the toilet bowl cleaner formulation for household use will be commercially sold as ready-to-use, concentrated versions are contemplated. Toilet bowl formulations for industrial and institutional use are preferably concentrated to about 10×. Industrial and institutional toilet bowl formulations can also be sold as ready-to-use.

In a further preferred embodiment, the sulfonated estolide formulation can be used in a glass cleaning application. Glass cleaner formulations of the present technology can exhibit, for example, a pH ranging from about 5 to about 13. Sulfonated estolide surfactants for use in glass cleaning applications can be in the range of about 0.1% to about 80% weight of active ingredient, preferably about 0.1 to about 35% or about 0.1% to about 20% for concentrated formulations or about 0.1% to about 15% for ready-to-use glass cleaning formulations. Concentrates can also be formulated for glass cleaning applications. Although most preferably the glass cleaner formulation for household use will be commercially sold as a ready-to-use formulation, concentrated versions are contemplated. Glass cleaner formulations for industrial and institutional use are preferably concentrated to about 20×, about 40×, or about 64×. Industrial and institutional toilet bowl formulations can also be sold as ready-to-use. Surprisingly, the active ingredient of the present technology can be diluted to 1% active weight in water and equal the performance of a commercial natural or "green" all surface cleaner on filming and streaking and equal another commercial glass cleaner on filming.

In a further preferred embodiment, one or more sulfonated estolide formulations of the present technology can be used in one or more bathroom cleaning applications, which could address, for example, soap scum removal or descaling. Proper wetting and solvency can greatly affect the efficacy of soap scum cleaning formulations. Bathroom cleaner formulations of the present technology can exhibit a pH ranging from about 2 to about 13. Sulfonated estolide surfactants in such soap scum removal or descaling applications of the present technology can be in the range from about 0.1% to about 80% based upon the weight of active ingredient, preferably about 0.1% to about 35%; or alternatively about 0.1% to about 20% for concentrated formulations; and alternatively of about 0.1% to about 15% for ready-to-use formulations. Unexpectedly, non-hydrolyzed sulfonated estolides of the present technology have exhibited superior lime soap dispersing properties than, for example, sodium coco methyl ester sulfonate, ALPHA-STEP MC-48 (from a stripped coconut source) and similar performance to a sodium C1618 (95/5 blend of C16 and 18 from a palm oil source) which is know to those skilled in the art as a good lime soap dispersant. Concentrates can also be formulated for bathroom cleaning applications. Although most preferably the bathroom cleaner household formulation will be commercially sold as a ready-to-use formulation, concentrated versions are contemplated. Bathroom cleaner formulations for industrial and institutional use are preferably concentrated to about 10×, about 20×, or about 40×. Industrial and institutional bathroom cleaner formulations can also be sold as ready-to-use.

In a further preferred embodiment, one or more sulfonated estolide formulations of the present technology can be used as an all-purpose general cleaner, for example, to use in one or more kitchen cleaning applications. All purpose cleaner formulations of the present technology can exhibit a pH ranging from about 5 to about 13. Sulfonated estolide surfactants in such general purpose cleaning applications of the present technology can be in the range from about 0.1% to about 80% based upon the weight of active ingredient, preferably about 0.1% to about 35%; or alternatively about 0.1% to about 20% for concentrated formulations; and alternatively of about 0.1% to about 15% for ready-to-use formulations. Concentrates can also be formulated for all-purpose cleaning applications. Although most preferably the general purpose cleaner formulation for household use will be commercially sold as a ready-to-use formulation, concentrated versions are contemplated. All-purpose cleaner formulations for industrial and institutional use are preferably concentrated to about 10×, about 20×, or about 40×. Industrial and institutional bathroom cleaner formulations can also be sold as ready-to-use.

In a further preferred embodiment, one or more sulfonated estolide formulations of the present technology can be used in at least one floor cleaning application. Floor cleaner formulations of the present technology can exhibit a pH ranging from about 2 to about 14. Sulfonated estolide surfactants in floor cleaning applications of the present technology can be in the range from about 0.1% to about 80% based upon the weight of active ingredient, preferably about 0.1% to about 35%; or alternatively about 0.1% to about 20% for concentrated formulations; and alternatively of about 0.1% to about 15% for ready-to-use formulations. Preferably, concentrated formulations are contemplated for both household and industrial and institutional applications. Floor cleaner formulations for household or industrial and institutional use are preferably concentrated to about 32×, about 64×, or about 128×. Either household or industrial and institutional floor cleaner formulations can also be sold as a ready-to-use formulation.

In a further aspect, the presently described technology can provide a carpet cleaning composition, comprising from about 5% to about 90% by weight of active sulfonated estolide as described in general Formula 1. Carpet cleaner formulations of the present technology can exhibit a pH ranging from about 2 to about 14. Sulfonated estolide surfactants in carpet cleaning applications of the present technology can be in the range from about 0.1% to about 80% based upon the weight of active ingredient, preferably about 0.1% to about 35%; or alternatively about 0.1% to about 20% for concentrated formulations; and alternatively of about 0.1% to about 15% for ready-to-use formulations. Preferably, concentrated formulations are contemplated for both household and industrial and institutional applications. Carpet cleaner formulations for household or industrial and institutional use are preferably concentrated to about 32×, about 64×, or about 128×. Either household or industrial and institutional floor cleaner formulations can also be sold as a ready-to-use formulation.

The general purpose, bathroom cleaning, toilet bowl cleaning, floor cleaning, glass cleaning, carpet cleaning and degreasing formulations of the present technology can be used in a variety of different delivery processes of forms such as Ready-To-Use ("RTU") formulations, dilutable, wipes, gels, pastes, slurries, powders, concentrates, on cleaning tools or apparatuses such as Swifter by P&G or Clorox Toilet Wand system etc. For example, the compositions of the present technology can take the form of a dilutable, that may be an isotropic liquid, a surfactant-structured liquid, a granular, spray-dried or dry-blended powder, a tablet, a paste, a molded solid, a water soluble sheet, put onto a wipe or other substrate, into a pouch which may be water soluble, or any form known to those skilled in the art. A "dilutable" composition is defined, for the purposes of this disclosure, as a product intended to be used by being diluted with water or a non-aqueous solvent by a ratio ranging from about 1:1 to about 1:150 to produce a liquor suitable for treating a surface. It is contemplated that concentrated compositions of the present technology could be sold in forms to be diluted by the end-consumer. Current commercial examples of such concentrated formulations include Clorox Pine Sol, Clorox Greenworks Dilutable concentrate, and other Industrial & Institutional (I&I) formulations which instruct end-consumers to dilute 1-5 oz. of the concentrated formulation to a final volume of one gallon prior to use. Concentrated formulations decrease packing requirements, comply with shelf-space requirements and decrease shipping costs—all of which have a positive environmental impact and cost. Sulfonated estolide surfactants as described herein can be used in the various formulations of the present technology in the range of about 0.1% to about 80% weight of active ingredient, preferably about 0.1% to about 35% or about 0.1 to about 20% for concentrated formulations or about 0.1% to about 15% for ready-to-use formulations. These formulations, in some embodiments, are stable with acidic and alkaline buffers, adjuvant/builders, peroxide, hypochlorite bleach, and other bleaching agents, among other components, additives, or ingredients.

The compositions of the present technology can take any of a number of forms and any of the different delivery systems that are currently known or to be developed in the future such as ready-to-use, dilutable, wipes, gels, pastes, slurries, concentrates, on cleaning tools or apparatuses such as Swifer by P&G or Clorox Toilet Wand system, for example.

The present technology may also be used to add detergency and other surfactant properties to bleach to constitute cleaning formulations, for example, bleach-based hard surface cleaners.

The formulations of the present technology may also be included in compositions utilizing a cleaning adjunct. Common cleaning adjuncts are identified in U.S. Pat. No. 7,326,675, col. 12, and PCT Publ. WO 99/05242 (Pages 29-56). Such cleaning adjuncts include, but are not limited to bleaches, dispersant polymers (e.g., from BASF Corp. or Rohm & Haas) other than those described above, hard water control, buffers, color speckles, silvercare, anti-tarnish and/or anti-corrosion agents, pigments, dyes, fillers, germicides, hydrotropes, anti-oxidants, enzyme stabilizing agents, pro-perfumes, carriers, processing aids, solvents, dye transfer inhibiting agents, brighteners, structure elasticizing agents, fabric softeners, anti-abrasion agents, derivatives thereof other fabric care agents, surface agents, and combinations thereof. Suitable examples of such other cleaning adjuncts and levels of use are found in U.S. Pat. Nos. 5,576,282, 6,306,812 B1 and 6,326,348 B1 and PCT Publ. WO99/05242. All the patents identified in this paragraph are incorporated by reference in their entireties with respect to their respective disclosures of adjuvants.

General Considerations for Cleaning Products

Desirable attributes of the present technology include, but are not limited to equal or superior cleaning performance when compared to other surfactants in comparable classic and "green" or natural formulations; and stability in ready-to-use and concentrated formulations; "green" or "eco-friendly" degradability; and improved cost of production.

The formulations of the present technology can involve one or more variants of general Formula 1 in combination with at least one carrier and, optionally, at least one additional component, such as at least one additive. For example, in some embodiments the present technology can also comprise at least one additional surfactant or at least one solvent. Still further embodiments can include, for example, an adjuvant or buffer as an additive or one or more additives (e.g., dyes, fragrances, hydrotropes). Still further embodiments can include, for example, a biocidal or disinfecting agent as an additive or one or more additives in addition to optional solvents and/or surfactants. Other formulations are also envisaged.

As will also be appreciated by at least those skilled in the art, a variety of carriers, vehicles, diluents, and the like are suitable for use in the practice of the present technology. Thus, it will also be appreciated that the terms "carrier", "vehicle", and/or "diluent" are to be considered non-exhaustive with respect to the present technology, and in describing the various formulations, applications, compositions thereof. For example, one or more carriers for use in practicing the present technology can include, but are not limited to, e.g., water, ethanol, or other low molecular weight alcohols. Carriers can comprise from about 0.1% to about 99.9% of weight of the formulation of the present technology.

For household, industrial and institutional cleaning products, both surfactants and solvents are important ingredients. Desirable attributes for such products include, for example, the ability to emulsify, suspend or penetrate greasy or oily soils and suspend or disperse particulates, in order to clean surfaces; and then prevent the soils, grease, or particulates from re-depositing on the newly cleaned surfaces.

It is also desirable to have the ability to control the foaming of one or more household, industrial and institutional products. Low foam is preferred, but consumers prefer to observe some amount of foam as an indication that the formula is working. For example, for hard surface cleaners, it is desirable to have the ability to wet various surface types and, couple or suspend soils, to leave the surface free from residue in the form of streaking and/or filming and to reduce the need for excessive wiping or and rinsing.

It is also desirable to have a hydrotropic ability in coupling the ingredients in formulations in order to reduce the need to add any or large amounts of hydrotrope ingredients. This hydrotropic ability also adds the benefit of being able to concentrate formulas beyond those typically found using traditional surfactants.

As a result, both concentrated and ready-to-use formulations of the present technology preferably have a viscosity of 1 centipoise to about 1500 centipoise, measured at 25° C. using a Brookfield Viscometer model DV-II+, using spindle #2, at a speed of 60 rpm; more preferably having a viscosity of 1 centipoise to about 400 centipoise, measured at 25° C. using a Brookfield Viscometer model DV-II+, using spindle #2, at a speed of 60 rpm. Interestingly, certain SHP, PEHP, or EHP formulations have been found to have lower viscosity than comparable formulations lacking these surfactants, such that these compositions function as viscosity reducers, which is very useful for making the contemplated more concentrated, (e.g. greater than about 5% surfactant active) cleaning formulations.

The sulfonated fatty acid products described herein can be incorporated into, for example, various compositions and used as surfactants, cleaners, wetters emulsifiers, rheological modifiers, solvents, release agents, lubrication agents, conditioners, and dispersants, hydrotropes, and the like. Such compositions can be used in household and industrial and institutional cleaning products.

In one embodiment, the present technology provides at least one hard surface cleaner composition comprising 0.1% to about 99.9% of sulfo-estolides of general Formula 1, but preferably in the range of about 0.1% to about 80%, with 1% to about 99.9% by weight of a carrier.

In another embodiment, the present technology provides at least one hard surface cleaner comprising about 0.1% to about 99.9% of sulfo-estolides of general Formula 1 and about 0.1% to about 99.9% by weight of at least one solvent.

In alternative embodiments, the formulations of the present technology can comprise about 0.1% to about 90%, about 0.1% to about 80%, about 0.1% to about 60%, about 0.1% to about 50%, about 0.1% to about 30%, about 0.1% to about 20% by weight of at least one solvent, and includes any percentage or range there between, including, but not limited to, increments of about 0.1, about 0.2, about 0.3, about 0.4, about 0.5, about 0.6, about 0.7, about 0.8, about 0.9 or about 1.0% and multiplied factors thereof, for example, about 1%, about 2%, about 5%, about 7%, about 10%, about 15%, about 18%, about 20%, about 25%, about 30%, about 35%, about 40%, about 45%, about 48%, about 50%, about 55%, about 60%, about 65%, about 70%, about 75%, about 80%, about 85%, about 90%, etc; as well as about 1×, about 2×, about 3×, about 4×, about 5×, about 10×, about 20×, about 50×, about 100×, about 150×, etc. for concentrate purposes.

Compositions of the present technology can also comprise about 0.1% to about 99% by weight of general Formula 1, preferably about 0.1% to about 80% by weight. Alternatively, general Formula 1 can be about 0.5% to about 99%, alternatively about 1.0% to about 99%, alternatively about 1.0% to about 80%, alternatively about 1.0% to about 70%, alternatively about 1.0% to about 60%, alternatively about 1.0% to about 60%, alternatively about 1.0% to about 50%, alternatively about 1.0% to about 40%, alternatively about 1.0% to about 30%, alternatively about 1.0% to about 20%, alternatively about 1.0% to about 10%, alternatively about 0.5% to about 20%, alternatively about 0.5% to about 10% by weight of the compositions, and include any range or percentage there between, including, but not limited to, additional increments of, for example, about 0.1, about 0.2, about 0.3, about 0.4, about 0.5, about 0.6, about 0.7, about 0.8, about 0.9 or about 1.0% and multiplied factors thereof, for example, about 0.5%, about 0.6%, about 0.8%, about 1.0%, about 2.0%, about 3%, about 4%, about 5%, about 8%, about 10%, about 15%, about 20%, about 25%, about 30%, about 35%, about 40%, about 45%, about 50%, etc.

In still further embodiments the present technology provides one or more hard or solid surface cleaning compositions having about 0.1% to about 99.9% by weight of general Formula 1, optionally, about 0.1% to about 90% by weight of at least one additional surfactant; and optionally, about 0.1% to about 99.9% by weight of at least one carrier. In alternative embodiments, such hard or solid surface cleaning composition can include about 5% to about 90%, about 10% to about 90%, about 15% to about 90%, about 20% to about 80% by weight of at least one solvent, and includes any percentage or range there between, including, but not limited to, increments of about 0.1, about 0.2, about 0.3, about 0.4, about 0.5, about 0.6, about 0.7, about 0.8, about 0.9 or about 1.0, about 2.5, about 5% and multiplied factors thereof, for example, about 1%, about 2%, about 2.5%, about 5%, about 7%, about 7.5%, about 10%, about 15%, about 18%, about 20%, about 25%, about 30%, about 35%, about 40%, about 45%, about 48%, about 50%, about 55%, about 60%, about 65%, about 70%, about 75%, about 80%, about 85%, about 90%, etc; as well as about 1×, about 2×, about 3×, about 4×, about 5×, about 10×, about 20×, about 50×, about 100×, about 150×, etc. for concentrate purposes. In still further alternative embodiments, the hard or solid surface cleaning composition can include at least one solvent, at least one additional additive, at least one adjuvant, at least one buffer or any combination thereof as described herein. Other combinations and additives are also envisaged for further embodiments of the present technology.

Exemplary Sulfo-Estolide Compositions

A wide variety of compositions can be made that include SE, PHSE, HSE, SHP, PEHP, EHP, or combinations of two or more or all of these, as described herein, with or without other ingredients some of which are specified below. Formulations are contemplated having about 0.1% to about 99.9% by weight of active composition of SE, PHSE, HSE, SHP, PEHP, and/or EHP, more preferably between about 1% and about 60% by weight, even more preferably between about 1% and about 30% by weight, with about 0.1% to about 99.9% by weight water and, optionally, other ingredients as described herein.

Surfactants

Suitable additional surfactants for use in the practice of present technology include, but are not limited to anionic surfactants, cationic surfactants, nonionic surfactants, ampholytic surfactants, zwitterionic surfactants, or combinations thereof. Mixtures of any two or more individually contemplated surfactants, whether of the same type or different types, are also envisaged. Suitable surfactants used in the present technology are also disclosed in PCT Application Serial No. PCT/US09/31608, which is incorporated herein by reference in its entirety.

Anionic Surfactants

"Anionic surfactants" are defined herein as amphiphilic molecules with an average molecular weight of less than about 10,000, comprising one or more functional groups that exhibit a net anionic charge when in aqueous solution. The anionic surfactant used in the present technology can be any substantially water soluble anionic surfactant. "Water soluble" surfactants are, unless otherwise noted, here defined to include surfactants which are soluble or dispersible to at least the extent of about 0.01% by weight in distilled water at 25° C. Another important class of anionic compounds is the water soluble salts, particularly the alkali metal salts, of organic sulfur reaction products having in their molecular structure an alkyl radical containing from about 6 to about 24 carbon atoms and a radical selected from the group consisting of sulfonic and sulfuric acid ester radicals.

Specific types of anionic surfactants are identified in the following paragraphs. At least in some embodiments, alkyl sulfates are preferred. In other embodiments, alkyl lactates are preferred. A less preferred anionic surfactant is linear alkyl benzene sulfonate or alkyl ether sulfates due to their higher foaming ability. Primary alkyl sulfates are represented by the formula:

$$R^2OSO_3M$$

where $R^2$ is a primary alkyl group of 8 to 18 carbon atoms. M is H or a cation, e.g., an alkali metal cation (e.g. sodium, potassium, lithium), or ammonium or substituted ammonium (e.g. methyl-, dimethyl-, and trimethyl ammonium cations and quaternary ammonium cations such as tetramethyl-ammonium and dimethyl piperidinium cations and quaternary ammonium cations derived from alkylamines such as ethylamine, diethylamine, triethylamine, and mixtures thereof, and the like). The alkyl group $R^2$ may have a mixture of chain lengths. It is preferred that at least two-thirds of the $R^2$ alkyl groups have a chain length of about 8 to about 14 carbon atoms. This will be the case if $R^2$ is coconut alkyl, for example. The solubilizing cation may be a range of cations which are in general monovalent and confer water solubility. An alkali metal, notably sodium, is especially envisaged. Other possibilities are ammonium and substituted ammonium ions, such as trialkanolammonium or trialkylammonium. For natural formulations, a natural alcohol is preferred for the alkyl group.

Alkyl ether sulfates are represented by the formula:

$$R^3O(CH_2CH_2O)_nSO_3M$$

where $R^3$ is a primary alkyl group of about 8 to about 18 carbon atoms, n has an average value in the range from about 1 to about 6 and M is a solubilizing cation. The alkyl group $R^3$ may have a mixture of chain lengths. It is preferred that at least two-thirds of the $R^3$ alkyl groups have a chain length of about 8 to about 14 carbon atoms. This will be the case if $R^3$ is coconut alkyl, for example. Preferably n has an average value of about 2 to about 5. For natural formulations, a natural alcohol is preferred for the alkyl group.

Other suitable anionic surfactants that can be used are alkyl ester sulfonate surfactants including linear esters of $C_8$-$C_{20}$ carboxylic acids (i.e., fatty acids) which are sulfonated with gaseous $SO_3$ according to "The Journal of the American Oil Chemists Society", 52 (1975), pp. 323-329 and is incorporated herein by reference. Suitable starting materials would include natural fatty substances as derived from tallow, palm oil, etc.

The preferred alkyl ester sulfonate surfactants, especially hard surface, comprise alkyl ester sulfonate surfactants of the structural formula:

$$R^3\text{—CH}(SO_3M)\text{-C}(O)\text{—}OR^4$$

where $R^3$ is a $C_8$-$C_{20}$ hydrocarbyl, preferably an alkyl or combination thereof $R^4$ is a $C_1$-$C_6$ hydrocarbyl, preferably an alkyl, or combination thereof, and M is a cation which forms a water soluble salt with the alkyl ester sulfonate. Suitable salt-forming cations include metals such as sodium, potassium, and lithium, and substituted or unsubstituted ammonium cations, such as monoethanolamine, diethanolamine, and triethanolamine. Preferably, $R^3$ is $C_{10}$-$C_{16}$ alkyl, and $R^4$ is methyl, ethyl or isopropyl. Especially preferred are the methyl ester sulfonates where $R^3$ is $C_{10}$-$C_{16}$ alkyl. Since the alkyl chain usually comes from a natural source, this molecule is preferred for natural based formulations.

Fatty acid ester sulfonates are represented by the formula:

$$R^4CH(SO_3M)CO_2R^5$$

where $R^4$ is an alkyl group of about 6 to about 16 atoms, $R^5$ is an alkyl group of about 1 to about 4 carbon atoms and M is a solubilizing cation. The group $R^4$ may have a mixture of chain lengths. Preferably at least two-thirds of these groups have about 6 to about 12 carbon atoms. This will be the case when the moiety $R^4CH(-)CO_2(-)$ is derived from a coconut source, for instance. It is preferred that $R^5$ is a straight chain alkyl, notably methyl or ethyl.

Alkyl benzene sulfonates are represented by the formula:

$$R^6ArSO_3M$$

where $R^6$ is an alkyl group of about 8 to about 18 carbon atoms, Ar is a benzene ring ($\text{—}C_6H_4\text{—}$) and M is a solubilizing cation. The group $R^6$ may be a mixture of chain lengths. A mixture of isomers is typically used, and a number of different grades, such as "high 2-phenyl" and "low 2-phenyl" are commercially available for use depending on formulation needs. A plentitude of commercial suppliers exist for these materials, including Stepan (Northfield, Ill.) and Witco (Greenwich, Conn.) Typically they are produced by the sulfonation of alkylbenzenes, which can be produced by either the HF-catalyzed alkylation of benzene with olefins or an $AlCl_3$-catalyzed process that alkylates benzene with chloroparaffins, and are commercially available, for example, by Petresa (Chicago, Ill.) and Sasol (Austin, Tex.). Straight chains of about 11 to about 14 carbon atoms are usually preferred.

Paraffin sulfonates having about 8 to about 22 carbon atoms, preferably about 12 to about 16 carbon atoms, in the alkyl moiety, are contemplated as additional surfactants to be added in certain compositions of the present technology. Paraffin sulfonates are usually produced by the sulfoxidation of petrochemically-derived normal paraffins. Hostapur SAS (available from Clariant located in Charlotte, N.C.) is a commercial example of a paraffin sulfonate.

Olefin sulfonates having about 8 to about 22 carbon atoms, preferably about 8 to about 16 carbon atoms, are also contemplated as additional surfactants to be added in certain compositions of the present technology. The olefin sulfonates are further characterized as having from 0 to 1 ethylenic double bonds; from 1 to 2 sulfonate moieties, of which one is a terminal group and the other is not; and 0 to 1 secondary hydroxyl moieties. U.S. Pat. No. 3,332,880 contains a description of suitable olefin sulfonates, and is incorporated herein by reference.

Thus, for additional examples of anionic surfactants, the cation can be any cation that forms a water-soluble salt such as alkali metals, e.g., sodium and potassium, and ammonium and substituted ammonium compounds, e.g., trialkylammonium and trialkylolammonium compounds. Specific examples of substituted ammonium compounds are triethylammonium, trimethylammonium, and triethanolammonium. Others examples will be apparent to those skilled in the art. One commercial example of an oelin sulfonate is Bio-Terge AS-40, which can be purchased from Stepan Company (Northfield, Ill.)

Sulfosuccinate esters represented by the formula:

$$R^7OOCCH_2CH(SO_3^-M^+)COOR^8$$

are also useful in the context of the present technology. $R^7$ and $R^8$ are alkyl groups with chain lengths of between about 2 and about 16 carbons, and may be linear or branched, saturated or unsaturated. A preferred sulfosuccinate is sodium bis(2-ethylhexyl) sulfosuccinate, which is commercially available under the trade name Aerosol OT from Cytec Industries (West Paterson, N.J.).

Organic phosphate based anionic surfactants include, for example, organic phosphate esters such as complex mono- or diester phosphates of hydroxyl-terminated alkoxide condensates, or salts thereof. Included in the organic phosphate esters are phosphate ester derivatives of polyoxyalkylated alkylaryl phosphate esters, of ethoxylated linear alcohols and ethoxylates of phenol. Also included are nonionic alkoxylates having a sodium alkylenecarboxylate moiety linked to a terminal hydroxyl group of the nonionic through an ether bond. Counterions to the salts of all the foregoing may be those of alkali metal, alkaline earth metal, ammonium, alkanolammonium and alkylammonium types.

Further fatty acid ester sulfonates are represented by the formula:

$$R^9CH(SO_3M)CO_2R^{10}$$

where the moiety $R^9CH(-)CO_2(-)$ is derived from a coconut or palm source and $R^{10}$ is either methyl or ethyl. Molecules derived from a natural source are preferred for a natural cleaning product.

Another class of anionic surfactants contemplated as additional surfactants to be added in certain compositions of the present technology is the alkyl alkoxylated sulfate surfactants which are water soluble salts or acids of the formula $RO(A)_m SO_3M$ where R is an unsubstituted $C_8$-$C_{24}$ alkyl or hydroxyalkyl group having a $C_8$-$C_{24}$ alkyl component, preferably a $C_8$-$C_{14}$ alkyl or hydroxyalkyl, more preferably $C_8$-$C_{15}$ alkyl or hydroxyalkyl, A is an ethoxy or propoxy unit, m is greater than zero, typically between about 0.5 and about 6, more preferably between about 0.5 and about 3, and M is H (i.e., hydrogen) or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include, but are not limited to ethanol-, triethanol-, methyl-, dimethyl-, or trimethylammonium cations and quaternary ammonium cations such as tetramethyl-ammonium and dimethyl piperidinium cations and those derived from alkylamines such as ethylamine, diethylamine, triethylamine, combinations and mixtures thereof. Surfactants are $C_{12}$-$C_{15}$ alkyl polyethoxylate (1.0) sulfate ($C_8$-$C_{10}$ E(1.0)M), $C_8$-$C_{10}$ alkyl polyethoxylate (2.2) sulfate, ($C_{12}$-$C_{15}$ E(2.25)M), $C_{12}$-$C_{15}$ alkyl polyethoxylate (3.0) sulfate ($C_{12}$-$C_{15}$ E(3.0)M), and $C_{12}$-$C_{15}$ alkyl polyethoxylate (4.0) sulfate ($C_{12}$-$C_{15}$ E(4.0)M), where M is conveniently selected from sodium, potassium, or ammonium or substituted-ammonium cation.

Other anionic surfactants useful for detersive purposes can also be included in the compositions of the present technology. These can include salts (including, for example, sodium, potassium, ammonium, and substituted ammonium salts such as mono-, di- and triethanolamine salts) of soap, $C_8$-$C_{22}$ primary or secondary alkanesulfonates, $C_8$-$C_{24}$ olefin sulfonates, sulfonated polycarboxylic acids prepared by sulfonation of the pyrolyzed product of alkaline earth metal citrates, for example, as described in British patent specification No. 1,082,179, which is incorporated herein by reference, $C_8$-$C_{24}$ alkypolyglycolethersulfates (containing up to about 10 moles of ethylene oxide); alkyl glycerol sulfonates, fatty acyl glycerol sulfonates, fatty oleoyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (especially saturated and unsaturated $C_{12}$-$C_{18}$ monoesters) and diesters of sulfosuccinates (especially saturated and unsaturated $C_6$-$C_{12}$ diesters), sulfates of alkylpolysaccharides such as the sulfates of alkylpolyglucoside (the nonionic non-sulfated compounds being described below), and alkyl polyethoxy carboxylates such as those of the formula $RO(CH_2CH_2O)_kCH_2COO-M+$ where R is a $C_8$-$C_{22}$ alkyl, k is an integer from 0 to 10, and M is a soluble salt-forming cation. Resin acids and hydrogenated resin acids are also suitable, such as rosin, hydrogenated rosin, and resin acids and hydrogenated resin acids present in or derived from tall oil. Further examples are described in "Surface Active Agents and Detergents" (Vol. I and II by Schwartz, Perry and Berch), which is herein incorporated by reference. A variety of surfactants are also generally disclosed in U.S. Pat. Nos. 3,929,678 5,929,022 and 6,949,498 which are incorporated herein by reference.

Other anionic surfactants contemplated for use with this formulation include isethionates, sulfated triglycerides, alcohol sulfates, ligninsulfonates, naphthelene sulfonates and alkyl naphthelene sulfonates, alkane sulfonates, alkyl diphenol disulfonates, sulfoacetates, olefin sulfonates, alkyl benzene sulfonates, alkyl sulfosuccinates, alkyl sulfomethylsuccinates, alkyl lactates, and the like. Additional anionic surfactants, falling into the general definition but not specifically mentioned above, should also be considered within the scope of the present technology.

Preferable anionic surfactants contemplated for use in the present compositions include alcohol ether sulfates, linear alkylbenzene sulfonates, alcohol sulfates, alkane sulfonates, alkyl diphenol oxide disulfonate, or combinations of two or more of these.

Cationic Surfactants

Specific cationic surfactants contemplated for use in the present compositions include ditallow dimethylammonium chloride (DTDMAC), fatty alkanolamides (FAA), and quaternized diesters of trialkanolamines and fatty acids. The proportions of cationic surfactants used in a formulation can range, for example, from about 0.1% to about 20% actives by weight, more preferably between about 1% and about 10% actives by weight, even more preferably between about 1% and about 5% actives by weight.

Cationic detersive surfactants suitable for use in the compositions of the present technology include those having one long-chain hydrocarbyl group. Examples of such cationic surfactants include the ammonium surfactants such as alkyldimethylammonium halogenides, and those surfactants having the formula:

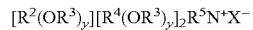

$[R^2(OR^3)_y][R^4(OR^3)_y]_2R^5N^+X^-$ where $R^2$ is an alkyl or alkyl benzyl group having from about 8 to about 18 carbon atoms in the alkyl chain, each $R^3$ is selected from the group consisting of —$CH_2CH_2$—, —$CH_2CH(CH_3)$—, —$CH_2CH(CH_2OH)$—, —$CH_2CH_2CH_2$—, and mixtures thereof; each $R^4$ is selected from the group consisting of $C_1$-$C_4$ alkyl, $C_1$-$C_4$ hydroxyalkyl, benzyl ring structures formed by joining the two $R^4$ groups, —$CH_2CHOH$—$CH(OH)C(O)R^6CH(OH)CH_2OH$ where $R^6$ is any hexose or hexose polymer having a molecular weight less than about 1000, and hydrogen when y is not 0; $R^5$ is the same as $R^4$ or is an alkyl chain where the total number of carbon atoms of $R^2$ plus $R^5$ is not more than about 18; each y is from 0 to about 10 and the sum of the y values is from 0 to about 15; and X is any compatible anion. The long chain cationic surfactant can also be the quaternized version of stearamidopropyl dimethylamine (e.g., stearamidopropyl trimethylamine chloride).

Preferred cationic surfactants are the water-soluble quaternary ammonium compounds useful in the present composition having the formula:

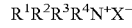

$R^1R^2R^3R^4N^+X^-$ where $R^1$ is $C_8$-$C_{16}$ alkyl, each of $R^2$, $R^3$ and $R^4$ is independently $C_1$-$C_4$ alkyl, $C_1$-$C_4$ hydroxyalkyl, benzyl, or —$(C_2H_4O)_xH$ where x has a value from 1 to 5, and X is an anion. In an embodiment, not more than one of $R^2$, $R^3$ or $R^4$ is benzyl. The preferred alkyl chain length for $R^1$ is $C_{12}$-$C_{15}$, particularly where the alkyl group is a mixture of chain lengths derived from coconut or palm kernel fat or is derived synthetically by olefin build up or OXO alcohols synthesis. Preferred groups for $R^2$, $R^3$, and $R^4$ are methyl and hydroxyethyl groups and the anion X may be selected from halide, methosulphate, acetate and phosphate ions.

Examples of suitable quaternary ammonium compounds for use here are: hexadecyl trimethyl ammonium chloride, also known as cetrimonium chloride, sold commercially as Ammonyx® CETAC by Stepan Co.; coconut trimethyl ammonium chloride or bromide; coconut methyl dihydroxyethyl ammonium chloride or bromide; decyl triethyl ammonium chloride; decyl dimethyl hydroxyethyl ammonium chloride or bromide; $C_{12-15}$ dimethyl hydroxyethyl ammonium chloride or bromide; coconut dimethyl hydroxyethyl ammonium chloride or bromide; myristyl trimethyl ammonium methyl sulphate; lauryl dimethyl benzyl ammonium chloride or bromide; lauryl dimethyl (ethenoxy)4 ammonium chloride or bromide; choline esters of formula $$R^1R^2R^3R^4N^+X^-$$

where $R^1$ is —$CH_2$—O—C(O)—($C_{12-14}$ alkyl) and $R^2$, $R^3$, and $R^4$ are methyl; and combinations of these. Additional examples include alkyl trimethyl ammonium quats, alkyl dimethyl benzyl quats, alkyl amido amine quats, dialkyl amido amine quats, dialkyl dimethyl ammonium quats, mono- or di-alkyl ester quats.

Other cationic surfactants useful here are also described in U.S. Pat. Nos. 4,228,044 and 5,929,022, which are, incorporated herein by reference.

Nonionic Surfactants

Examples of suitable nonionic surfactants include alkyl polyglucosides, alkyl carboxylic acid esters, alcohol alkoxylates, alkyl phenol alkoxylates nonylphenol ethoxylates, and alkyl ethanolamides, alkyl esters, alkyl carboxylic esters, combinations thereof and derivative thereof. Preferred nonionic surfactants are alcohol ethoxylates and/or propoxylates which are commercially available with a variety of fatty alcohol chain lengths and a variety of ethoxylation degrees. For natural based cleaners, the use of a natural alcohol can be used.

Particularly suitable to be used in the practice of the present technology as nonionic surfactants are those having an HLB (hydrophilic-lipophilic balance) below about 16, more preferably below about 13. The hydrophobic (lipophilic) moiety may be aliphatic or aromatic in nature and the length of the polyoxyethylene group which is condensed with any particular hydrophobic group can be readily adjusted to yield a water-soluble compound having the desired degree of balance between hydrophilic and hydrophobic elements. For natural based formulations, a preferred alcohol would come from a natural source.

Especially preferred nonionic surfactants of this type are the $C_9-C_{15}$ primary alcohol ethoxylates containing 2-12 moles of ethylene oxide per mole of alcohol, particularly the $C_9-C_{11}$ primary alcohols containing about 2 to about 8 moles of ethylene oxide per mole of alcohol. One suitable example of such a surfactant is a $C_{9-11}$ polyalkoxylated aliphatic base with 6 moles of ethylene oxide, sold commercially for example as BIO-SOFT N91-6 by Stepan Company (Northfield, Ill.).

Another preferred class of nonionic surfactants for use in the practice of the present technology are alkyl polyglucoside compounds of the formula:

$$RO—(C_nH_{2n}O)_tZ_x$$

where Z is a moiety derived from glucose; R is a saturated hydrophobic alkyl group that contains from about 8 to about 18 carbon atoms; t is from 0 to 10 and n is 2 or 3; x is an average value from 1.3 to 4, the compounds including less than 10% unreacted fatty alcohol. Preferable alkyl polyglucosides for natural cleaning products are made from naturally derived alkyl substituent. Compounds of this type and are disclosed in U.S. Pat. Nos. 5,776,872; 5,883,062; and 5,906,973, which are all incorporated herein by reference. These surfactants are especially preferred in a natural based cleaner.

Other suitable as nonionic surfactants are poly hydroxy fatty acid amide surfactants of the formula:

$$R^2—C(O)—N(R^1)—Z$$

where $R^1$ is H, or $R^1$ is $C_{1-4}$ hydrocarbyl, 2-hydroxyethyl, 2-hydroxypropyl or a mixture thereof, $R^2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof. Preferably, $R^1$ is methyl, $R^2$ is a straight $C_{11-15}$ alkyl or alkenyl chain such as coconut alkyl or mixtures thereof, and Z is derived from a reducing sugar such as glucose, fructose, maltose, lactose, in a reductive amination reaction. Those made from a natural alkyl group are preferred for natural based cleaners.

Preferred nonionics are amine oxide surfactants. The compositions of the present technology may comprise amine oxide in accordance with the formula:

$$R^1(EO)_x(PO)_y(BO)_zN(O)(CH_2R')_2.H_2O$$

In general, it can be seen that the preceding formula provides one long-chain moiety $R^1(EO)_x(PO)_y(BO)_z$ and two short chain moieties, —$CH_2R'$. R' is preferably selected from hydrogen, methyl and —$CH_2OH$. In general R' is a primary or branched hydrocarbyl moiety which can be saturated or unsaturated, preferably, R' is a primary alkyl moiety. When x+y+z=0, R' is a hydrocarbyl moiety having a chain length of from about 8 to about 18. When x+y+z is different from 0, R' may be somewhat longer, having a chain length in the range $C_{12}-C_{24}$. The general formula also encompasses amine oxides where x+y+z=0, R' is $C_8-C_{18}$, R' is H and q=from 0 to 2, preferably 2. These amine oxides are illustrated by $C_{12-14}$ alkyldimethyl amine oxide, hexadecyl dimethylamine oxide, octadcylamine oxide and their hydrates, especially the dihydrates as disclosed in U.S. Pat. Nos. 5,075,501 and 5,071,594, which are incorporated herein by reference.

The presently described technology also encompasses amine oxides as a nonionic surfactant, where x+y+z is different from zero, specifically x+y+z is from about 1 to about 10, and R' is a primary alkyl group containing about 8 to about 24 carbons, preferably from about 12 to about 16 carbon atoms. In these embodiments y+z is preferably 0 and x is preferably from about 1 to about 6, more preferably from about 2 to about 4; EO represents ethyleneoxy; PO represents propyleneoxy; and BO represents butyleneoxy. Such amine oxides can be prepared by conventional synthetic methods, e.g., by the reaction of alkylethoxysulfates with dimethylamine followed by oxidation of the ethoxylated amine with hydrogen peroxide.

In certain of the preferred embodiments of the present technology in which R' is H, there is some latitude with respect to having R' slightly larger than H. Specifically, the presently described technology further encompasses embodiments where R'=$CH_2OH$, such as hexadecylbis(2-hydroxyethyl)amine oxide, tallowbis(2-hydroxyethyl)amine oxide, stearylbis(2-hydroxyethyl)amine oxide and oleylbis(2-hydroxyethyl)amine oxide.

Preferred amine oxides for use in the presently described technology herein include for example, decyl amine oxide, decyl amido amine oxide, coco or lauryl amine oxide and coco or lauryl amido amine oxide. Other preferred commercially available amine oxides are produced by a number of suppliers, including Stepan Company (Northfield, Ill.), such as AMMONYX DO, AMMONYX LO Special, AMMONYX LMDO. Amine oxides made from natural alkyl groups and are preferred for natural cleaning products.

Other nonionic surfactants include alkyl amine ethoxylates and alkyl lactyl lactates. Other examples and descriptions of nonionic surfactants can be found within U.S. Pat. No. 6,048,836 which is incorporated herein by reference.

Ampholytic Surfactants

Ampholytic surfactants (also including those surfactants known as amphoteric surfactants) can be broadly described as derivatives of aliphatic or aliphatic derivatives of heterocyclic secondary and tertiary amines, in which the aliphatic radical may be straight chain or branched and where one of the aliphatic substituents contains from about 8 to about 18 carbon atoms and at least one contains an anionic water-solubilizing group, for example, carboxy, sulfo, sulfato, phosphato, or phosphono surfactants include fatty amine oxides and fatty amidopropylamine oxides. See e.g., U.S. Pat. No. 3,664,961, which provides specific examples of ampholytic surfactants and is incorporated herein by reference). At least one suitable example is cocoamidopropyl betaine also known as coco betaine. Some representative examples include, but are not limited to amine oxides, amidopropyl amine oxides, betaines, amidopropyl betaines, sulfobetaines, hydroxysultaines, amphoacetates, amphopropionates, alkyl amines, organic diamines. Ampholytic surfactants can be used at a level from about 1% to about 50%, more preferably from about 1% to about 10%, even more preferably between about 1% and about 5% of one or more formulations of the present technology, by weight of actives.

Zwitterionic Surfactants

Zwitterionic surfactants can be broadly described as derivatives of aliphatic quaternary ammonium and phosphonium or tertiary sulfonium compounds, in which the cationic atom may be part of a heterocyclic ring, and in which the aliphatic radical may be straight chain or branched, and where one of the aliphatic substituents contains from about 3 to 18 carbon atoms, and at least one aliphatic substituent contains an anionic water-solubilizing group, e.g., carboxy, sulfo, sulfato, phosphato, or phosphono. See e.g., U.S. Pat. No. 3,664,961, which provides specific examples of zwitterionic surfactants and is incorporated herein by reference. Some representative examples include, but are not limited to betaines, sulfobetaines, imidazolines and propinates. Zwitterionic surfactants can be used as from about 1% to about 50%, more preferably from about 1% to about 10%, even more preferably from about 1% to about 5% by weight of the active formulation of the present technology.

Mixtures of Surfactants

Mixtures of any two or more individually contemplated surfactants, whether of the same type or different types, are contemplated herein.

To make a "green" formula, the surfactants should be ultimately biodegradable and have a low or minimal environmental impact. To meet consumer perceptions and reduce the use of petrochemicals, a "green" or natural formula may also advantageously be limited to the use of renewable hydrocarbons, such as vegetable or animal fats and oils, in the manufacture of surfactants.

In addition to the surfactants as previously described, a composition commonly contains other ingredients for various purposes. Some of those ingredients are also described below.

The one or more additional ingredients/components include, but are not limited to, alcohol ethoxylate, amine oxide, alkyl polyglucosides, alcohol sulfates, alkyl ester sulfonates, alkane sulfonates, alkyl diphenyl oxide disulfonates, betaines, nonylphenol ethoxylates, amides, and alkyl quaternary ammonium compounds. Included surfactants for hard surface cleaning formulations are known to those in the art. For natural formulations or "green" or "eco-friendly" formulations, the additional ingredients/components can be derived from a natural source and contain a biorenewable carbon index greater than about 75%. Biorenewable Carbon Index (BCI) is a value based on the percent carbon derived from biorenewable resources. Biorenewable is defined as originating from animal, plant or marine material. BCI is calculated by taking the number of biorenewable carbons divided by the total number of carbons from the idealized molecule. Examples of naturally derived surfactants include, but are not limited to alkyl polyglucosides, sulfonated methyl esters, amine oxides, alcohol sulfates and derivatives thereof.

Mixtures of any two or more individually contemplated surfactants, whether of the same type or different types, are envisaged. Additional surfactants can comprise about 0.1% to about 50% of the active weight in concentrated formulations, but preferably about 0.1% to about 30%, or about 0.1% to about 20% active weight in concentrated formulations. For ready-to-use formulations, additional surfactants can be from about 0.1% to about 20% of the of active weight, but preferably about 0.1% to about 10% of active weight.

Solvents

Solvents are often used in hard surface cleaners to prevent streaking or clouding the surface after cleaning. The present technology does not need in all embodiments or aspects the addition of a solvent, however, one may be optionally included in such formulations. For a natural hard surface cleaning formulation, preferably, any solvent added to the present technology would be limited to natural solvents. Examples of natural solvents contemplated for use in the practice of the present technology include, but are not limited to propylene glycol, 1,3-propane diol, sorbitol, alkyl lactyl lactates, propylene glycol, ethanol, glycerol, d-limonene, pine oil, combinations thereof, or derivatives thereof. Synthetic solvents can also be used in the practice of the present technology, such as, oxygen-containing solvents that are aliphatic alcohols of up to about 8 carbon atoms, alternatively tertiary alcohols of up to about 8 carbon atoms; aromatic-substituted alcohols; alkylene glycols of up to about 6 carbon atoms; polyalkylene glycols having up to 6 carbon atoms per alkylene group; mono- or dialkyl ethers of alkylene glycols or poly-alkylene glycols having up to about 6 carbon atoms per glycol group and up to about 6 carbons atoms in each alkyl group; mono- or diesters of alkylene glycols; or polyalkylene glycols having up to 6 carbon atoms per glycol group and up to about 6 carbon atoms in each ester group are contemplated for use in one or more embodiments of the present technology. Further examples of synthetic solvents contemplated for use in practicing the present technology include, but are not limited to low molecular weight alcohols such as isopropanol, butanol, methanol, ethanol and the like; glycols such as propylene glycol, hexylene glycol, ethylene glycol and the like; alkanols; glycol ethers such as ethylene glycol butyl ether, diethylene glycol butyl ether, propylene glycol n-butyl ether, dipropylene glycol n-butyl ether, dipropylene glycol methyl ether, among others; ketones, derivatives thereof, or combinations thereof. Additional examples of solvents contemplated herein, include, but are not limited to t-pentyl alcohol, 2,3-dimethyl-2-butanol, benzyl alcohol, propylene glycol mono-n-butyl ether, dipropylene glycol mono-n-butyl ether, propylene glycol mono-n-propyl ether, dipropylene glycol mono-n-propyl ether, diethylene glycol mono-n-butyl ether, diethylene glycol monomethyl ether, dipropylene glycol monomethyl ether, triethylene glycol, propylene glycol monoacetate, and dipropylene glycol monoacetate, ethers, derivatives thereof or combinations, thereof. Moreover further solvents for hard surface cleaning formulations of the present technology can be found in the fragrance section herein. Due to their hydrophobic nature, essential oils can facilitate grease cutting and solubilization and therefore improve cleaning.

Some preferred solvents for use in the present technology include, for example, the natural based solvents such as ethanol, glycerol, d-limonene or pine oil. Other preferred synthetic solvents include, for example, hexylene glycol, ethylene glycol butyl ether, diethylene glycol butyl ether, dipropylene glycol methyl ether, propylene glycol mono-n-butyl ether, dipropylene glycol mono-n-butyl ether, and the like.

In general with respect to formulations of the present technology, any solvent or mixture thereof can constitute about 0.1% to about 50% weight of the total composition in concentrated formulations, but alternatively about 0.1% to about 30% weight of the total composition, or alternatively about 0.1% to about 20% weight of the total composition. For ready-to-use formulations, additional surfactants will range from about 0.1% to about 20% of total composition weight, or alternatively about 0.1% to about 15% by weight of the total composition.

Solvents can have a detrimental effect on the environment. Certain solvents to be avoided in some embodiments of the present technology are those classified as a hazardous air pollutant or a volatile organic compound (also known as "VOC"). By decreasing solvent content (specifically volatile organic compound content), formulations of the present technology can potentially qualify to be certified as "environmental preferable" products by non-profit or governmental organizations and/or standard setting bodies.

Further Additives/Components

Other ingredients that can be included in one or more compositions or formulations of the present technology include, for example, chitosan, polymers, natural fragrances (that optionally contain ingredients such as aldehydes, ketones, esters, and alcohols); other carriers; hydrotropes; processing aids; dyes; pigments; solvents; bleaches; bleach activators; or peroxides, and thickening agents, among others. Any ingredient in this section would comprise from about 0.1% to about 10% weight of the total composition, and more preferably about 0.1% to about 5%% weight of the total composition.

Fragrances

Optionally, compositions of the present technology can contain additional fragrances containing d-limonene or lemon oil or other natural essential oils. Lemon oil or d-limonene can enhance the cleaning performance characteristics of the presently described cleaning compositions to allow suitable consumer performance with natural ingredients while utilizing a minimum of ingredients. Lemon oil and d-limonene compositions include mixtures of terpene hydrocarbons obtained from the essence of oranges, for example, cold-pressed orange terpenes and orange terpene oil phase sans fruit juice, or the mixture of terpene hydrocarbons expressed from lemons and grapefruit. The essential oils may contain minor non-essential amounts of hydrocarbon carriers. Suitably, the fragrance contains lemon oil or d-limonene in the cleaning composition in an amount ranging from about 0.01 to about 0.50 weight percent of the total composition, alternatively about 0.01 to about 0.40 weight percent of total composition, or about 0.01 to about 0.30 weight percent of the total composition, alternatively about 0.01 to about 0.20 weight percent of the total composition, alternatively about 0.01 to about 0.10 weight percent of the total composition, alternatively about 0.5 to about 1.0 weight percent of the total composition, alternatively about 0.05 to about 0.40 weight percent of the total composition, alternatively about 0.05 to about 0.30 weight percent of the total composition, alternatively about 0.05 to about 0.25 weight percent of the total composition, alternatively about 0.05 to about 0.20 weight percent of the total composition, alternatively about 0.05 to about 0.10 weight percent of the total composition. Other essential oils are described in U.S. Pat. No. 6,048,836, which is incorporated herein by reference.

Buffers

To practice the present technology in the various cleaning applications described herein, it may be necessary to adjust the pH. It is contemplated that the addition of a buffer will decrease or increase the pH of sulfonated estolide formulations. The use of the term "buffer" herein refers to acid or alkaline agents used for adjusting the pH to a desired or preferred range for cleaning the particular target soils or dirt.

When it is desirable to practice the present technology using an acidic formulation, an additional acidic buffer can be added or incorporated to lower the pH. Not wanting to be bound by any particular theory, acidic formulations are expected to be highly effective against mineral deposits and soap scum. The acidic buffer can be derived from natural or synthetic sources. Examples of natural acidic buffers suitable for use in the practice of the present technologyinclude, but are not limited to 2-hydroxycarboxylic acids, such as, tartaric acid, citric acid, malic acid, mandelic acid, glycolic acid, lactic acid, combinations thereof; or derivatives thereof. Examples of synthetic acidic buffers include, but are not limited to oxalic acid, lactic acid, sulfamic acid, adipic acid, hexanoic acid, glycolic acid, formic acid, acetic acid, propionic acid, butyric acid, gluconic acid, combinations thereof; or derivatives thereof, for example, peroxyacetic acid. Further examples of acidic buffers include strong mineral acids. Examples of strong mineral acids include, but are not limited to hydrochloric acid, nitric acid, phosphoric acid, sulfuric acid, sulfamic acid, boric acid, hydrofluoric acid, hydrobromic acid, derivatives thereof, or combinations thereof.

In at least one further embodiment of the present technology, when it is desirable to practice the present technology using an alkaline formulation, an additional alkaline buffer can be added or incorporated to raise the pH. In general, cleaning performance on greases, oily and waxy soils increases with increasing alkalinity. Performance can be enhanced in alkaline environments because the alkaline environment saponifies greases and neutralizes acid solids. Additional alkalinity can also modulate formulation evaporation rates, formulation viscosity, formulation surface penetration and may affect microemulsion stabilization; all of which may affect cleaning performance. The alkaline buffer can be derived from natural or synthetic sources. Examples of alkaline buffers include, but are not limited to ammonium and alkaline earth metal hydroxides including, but not limited to sodium hydroxide, potassium hydroxide, ammonium hydroxide; alkali metal carbonates; alkali metal bicarbonates; alkali metal and alkaline earth salts of silicates, such as sodium metasilicate; borates; ammonium or alkaline earth carbamates; guanidine derivatives; alkoxylalkylamines; alkyleneamines; alkanolamines; ammonium carbonates; ammonium bicarbonates; ethylenediaminetetraacetic acids; trialkyl salts of nitrilotriacetic acids; phosphates; combinations thereof; or derivatives thereof.

Adjuvants/Builders

Adjuvants/builders can also be included in one or more compositions of the present technology. Adjuvant/builders can supply alkalinity, further buffer the desired formulation pH, saponify greases, add detergency, peptize soil and/or inhibit corrosion. Examples of some preferred adjuvants include, but are not limited to aluminosilicate materials, silicates, polycarboxylates, carbonates, bicarbonates, sodium, potassium and ammonium salts and combinations thereof, materials such as ethylenediamine tetraacetate, metal ion sequestrants such as aminopolyphosphonates, particularly ethylenediamine tetramethylene phosphonic acid and diethylene triamine pentamethylenephosphonic acid, derivatives thereof, or combinations thereof. Other contemplated adjuvants/builders can include, but are not limited to chelating agents, for example, trisodium ethylenediamine disuccinate, glutamic acid, NN diacetic acid, tetra sodium salt, sodium gluconate, polyaspartic acid, polyamino acid, polysuccinates, tetrapotassium tripolyphosphate, disodium ethanoldiglycine, trisodium salt of methyl glycinediacetic acid, sodium nitilotriacetate, ethylenediamine tetraacetic acid and its salts, phosphates, tetrapotassium pyrophosphate, sodium tripolyphosphate, and citrates; acidifiers, for example, citric acid, glycolic acid, sulfamic acid, phosphoric acid, or oxalic acid; alkali, e.g., sodium metasilicate, sodium carbonate, sodium sesquicarbonate, sodium hydroxide, or triethanolamine, derivatives thereof, or combinations thereof. Though less preferred for obvious environmental reasons, phosphate adjuvants/builders could also be used in compositions of the present technology. In at least one preferred embodiment, sodium citrate is used as the adjuvant/builder.

Additionally, the practice of the present technology can also use suitable polycarboxylate adjuvants/builders that can include, but are not limited to citric acid, preferably in the form of a water-soluble salt, and derivatives of succinic acid of the following formula:

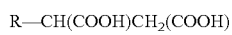

where R is $C_{10-20}$ alkyl or alkenyl, preferably $C_{12-16}$, or where R can be substituted with hydroxyl, sulfo sulfoxyl or sulfone substituents. Some specific examples include lauryl succinate, myristyl succinate, palmityl succinate 2-dodecenylsuccinate, or 2-tetradecenyl succinate. Succinate adjuvants are preferably used in the form of their water-soluble salts, including sodium, potassium, ammonium or alkanolammonium salts. Other suitable polycarboxylates are oxodisuccinates and mixtures of tartrate monosuccinic and tartrate disuccinic acid, as described in U.S. Pat. No. 4,663,071, incorporated by reference herein.

For liquid non-concentrate compositions, the adjuvants/builders typically comprise from about 0.1% to about 50% weight of the total composition, alternatively between about 0.1% to about 30% weight of the total composition, alternatively between about 0.1% to about 15% weight of the total composition. Other adjuvants are described in PCT Publ. WO 99/05242 and U.S. Pat. No. 5,929,022 (classified therein as "builder"), which are incorporated herein by reference.

Chelating agents in the amounts of about 0.1% to about 20% weight of the total composition, more preferably about 0.1% to about 10% by weight of the total composition and even more preferably from about 0.1% to about 3% by weight of the total composition are also contemplated as an optional ingredient for use in practicing the present technology. See e.g., U.S. Pat. No. 5,929,022; column 10, 1st paragraph to column 10, end of 2nd paragraph, for other examples of suitable chelating agents for use in the practice of the present technology.

Thickeners

Certain cleaning applications may require a viscous ready-to-use formulation of the present technology to obtain the best cleaning performance. Viscous formulations have improved properties for cleaning certain surfaces, for example, vertical walls or vertical surfaces on toilet bowls. Viscous formulations are able to contact the surface to be cleaned for a longer period of time which increases cleaning performance and ease of consumer use. Thickeners can be added to the formulations of the present technology to obtain viscous formulations. Typical thickeners for hard surface cleaners are known to those in the art, for example, cellulosic and xantham gum. For natural formulations, preferred thickeners include polymeric cellulosics and guar gum.

Disinfecting Agents

In some embodiments of the present technology, one or more disinfecting agents can be included. For example, natural essential oils are contemplated as disinfecting agents. Again not wanting to be bound by any particular theory, it is believed that certain natural essential oils and actives thereof act as protein denaturing agents. Also, certain natural essential oils and actives thereof are compounds which contribute to the safety profile of a composition when it is used to disinfect a surface. A further advantage of certain natural essential oils and actives thereof is that they impart pleasant odor to a composition without the need of adding a perfume. Indeed, it is believed that by combining certain natural essential oils or an active thereof with a surfactant and a chelant, in a composition of the present technology, allows them to deliver not only excellent disinfecting properties on surfaces to be treated, but also good scent while being safe to those surfaces.

Such essential oils for use in the practice of the present technology include, but are not limited to those obtained from thyme, lemongrass, citrus, lemons, oranges, anise, clove, aniseed, pine, cinnamon, geranium, roses, mint, lavender, citronella, eucalyptus, peppermint, camphor, sandalwood, rosmarin, vervain, fleagrass, lemongrass, ratanhiae, cedar, or mixtures thereof. Some preferred antimicrobial essential oils to be used herein are thyme oil, clove oil, cinnamon oil, geranium oil, eucalyptus oil, peppermint oil, mint oil, or mixtures thereof. Actives of essential oils to be used herein include, but are not limited to, thymol (present for example in thyme), eugenol (present for example in cinnamon and clove), menthol (present for example in mint), geraniol (present for example in geranium and rose), verbenone (present for example in vervain), eucalyptol and pinocarvone (present in eucalyptus), cedrol (present for example in cedar), anethol (present for example in anise), carvacrol, hinokitiol, berberine, ferulic acid, cinnamic acid, methyl salycilic acid, methyl salycilate, terpineol and mixtures thereof. Preferred actives of essential oils to be used herein are thymol, eugenol, verbenone, eucalyptol, terpineol, cinnamic acid, methyl salycilic acid and/or geraniol.

Typically, the certain natural essential oil or actives thereof or mixture thereof is present in the composition at a level of at least about 0.003% by weight of the total composition, preferably from about 0.006% to about 15% by weight of the total composition, more preferably from about 0.1% to about 4% by weight of the total composition and most preferably of from about 0.03% to about 2% by weight of the total composition.

Biocidal Agents

A typical antimicrobial composition comprising Formula 1 can include, for example, components such as one or more biocidal agents, one or more builders, one or more surfactants, one or more solvents, one or more additives, one or more vehicles, or a combination thereof. In at least one embodiment, the antimicrobial composition comprises from about 1% to about 99.9% of general Formula I, from about 0.001% to about 40% by weight of at least one biocidal agent, about 0% to about 40% of at least one additional surfactant; from about 1% to about 99% by weight of at least one vehicle; and from about 0% to about 40% by weight of at least one additional component.

Further, the antimicrobial agent comprises about 1% to about 99% by weight of a vehicle, preferably water. The compositions of the present technology can be prepared, for example, in a solid, gel, suspension, slurry, microemulsion, liquid, or powdered form or any other suitable form using different delivery vehicles, and can be prepared, for example as a ready-to-use or dilutable concentrate product. Whether in a ready-to-use form or a dilutable concentrate, the end use concentration of the components are equivalent. A dilutable concentrate must first be diluted in a suitable diluent to obtain the end use concentration. The delivery vehicles for a liquid form composition can be any diluent system known in the art. Examples of suitable diluents include, but are not limited to, water, glycols (preferably propylene glycol), alcohols (e.g., isopropanol, ethanol, or methanol), other polar solvents known in the art, and mixtures thereof. Placement of the compositions of the present technology upon a substrate, such as a wipe, fabric, cloth, among others use also envisaged.

An embodiment of the present technology can contain one or more biocidal agents, or a combination thereof as an additional additive/component. In at least one embodiment, the antimicrobial composition comprises from about 1% to about 99.9% of the general Formula 1, from about 0.001% to about 40% by weight of at least one biocidal agent. In additional embodiments, the antimicrobial compositions of the present technology can include from about 0.001% to about 30% by weight of at least one biocidal agent, alternatively about 0.01% to about 20%, alternatively about 0.001% to about 10%, alternatively about 0.01% to about 5%, alternatively about 0.01% to about 40%, alternatively about 0.1% to about 30%, alternatively about 0.5% to about 20% by weight of at least one biocidal agent, and includes percentages and ranges there between, in additional increasing or decreasing increments of, for example, about 0.1, about 0.2, about 0.3, about 0.4, about 0.5, about 0.6, about 0.7, about 0.8, about 0.9 or about 1.0% about 2.5%, about 5% and multiplied factors thereof (e.g., about 1×, about 5×, about 10×, about 50×, about 100×, or greater).

In alternative embodiments, the antimicrobial composition can further include from about 0.1% to about 40%, from about 1% to about 40%, from about 1% to about 30%, from about 1% to about 20%, from about 1% to about 10% by weight of at least one additional surfactant, and may additionally include any range and percentage there between, including, but not limited to, for example, increments of about 0.1, about 0.2, about 0.3, about 0.4, about 0.5, about 0.6, about 0.7, about 0.8, about 0.9 or about 1.0% and multiplied factors thereof.

Further, the antimicrobial composition can further include optionally about 0% to about 10% by weight of at least one solvent, alternatively from about 0.1% to about 10% of at least one solvent, alternatively from about 0.1% to about 5% of at least one solvent, alternatively from about 1% to about 5% of at least one solvent, and may include ranges there between, including, but not limited to, increasing or decreasing increments of about 0.1, about 0.2, about 0.3, about 0.4, about 0.5, about 0.6, about 0.7, about 0.8, about 0.9 or about 1.0%, about 2.5%, about 5% and multiplied factors thereof, for example, about 0.001%, about 0.005%, about 0.008%, about 0.01%, about 0.03%, about 0.05%, about 0.06%, about 0.1%, about 0.5%, about 0.8%, about 1.0%, about 2.0%, about 3%, about 4%, about 5%, about 8%, about 10%, about 12%, about 15%, about 20%, about 25%, about 30%, and the like.

The contemplated compositions containing the present technology inclusive of a biocidal agent are compositions that can reduce or inhibit the growth of or kill a biocidal target. "Biocidal targets" are organisms targeted to be reduced, inhibited, prevented or killed by an antimicrobial composition. These organisms include, for example, green and blue-green algae, gram negative and gram positive bacteria, enveloped and non-enveloped viruses, as well as fungi, including molds and yeasts.

One or more biocidal agents suitable for use in the practice of the present technology, include, but are not limited to ammonium quaternaries, e.g., 1,3-dibromo-5,5-dimethylhydantoin, 1,3-dibromo-5-ethyl-5-methylhydantoin, 1,3-dibromo-5-n-propyl-5-methylhydantoin, 1,3-dibromo-5-isopropyl-5-methylhydantoin, 1,3-dibromo-5-n-butyl-5-methylhydantoin, 1,3-dibromo-5-isobutyl-5-methylhydantoin, 1,3-dibromo-5-sec-butyl-5-methylhydantoin, 1,3-dibromo-5-tert-butyl-5-methylhydantoin, and mixtures thereof. Of these biocidal agents, 1,3-dibromo-5-isobutyl-5-methylhydantoin, 1,3-dibromo-5-n-propyl-5-methylhydantoin, and 1,3-dibromo-5-ethyl-5-methylhydantoin are, respectively, preferred, more preferred, and even more preferred members of this group from a cost effectiveness standpoint. Other suitable biocidal agent can also include, for example, n-alkyl dimethyl benzyl ammonium chloride; n-alkyl dimethyl ethylbenzyl ammonium chloride; dialkyl dimethyl ammonium chloride (for example didecyl dimethyl ammonium chloride or dioctyl dimethyl ammonium chloride), and mixtures thereof. Further examples can also include phenolics, iodophors, pine oil, methyl salicylate, morpholine, silver, copper, or bromine.

Suitable biocidal agents can also include quaternary ammonium compounds, or "quats." Any quat can be used in the presently described technology. Preferably, the quats utilized in the practice of the present technology exhibit biocidal activity or are of biocidal in nature. Examples of quats include, for example, alkyl ammonium halides such as cetyl trimethyl ammonium bromide, alkyl aryl ammonium halides, N-alkyl pyridinium halides such as N-cetyl pyridinium bromide, among others. At least one suitable type of quat includes, for example, those in which the molecules contain amine, ether or ester linkages such as octyl phenoxy ethoxy ethyl dimethyl benzyl ammonium chloride, N-(laurylcocoaminoformylmethyl)-pyridinium chloride, among others. Other biocidal agents or activators that can be used in combination with quats or other biocidal ingredients, for example, include hydrogen peroxide and its derivatives such as peracetic acid, and certain organic acids such as glycolic acid or lactic acid.

Another type of quat suitable for use in practice of the present technology includes, for example, those in which the hydrophobic radical is characterized by a substituted aromatic nucleus, as in the case of lauryloxyphenyltrimethyl ammonium chloride, cetylaminophenyltrimethyl ammonium methosulfate, dodecylphenyltrimethyl ammonium methosulfate, dodecylbenzyltrimethylammonium chloride, chlorinated dodecylbenzyltrimethyl ammonium chloride, and the like. Further examples of quats include, but are not limited to, didecyl dimethyl ammononium chloride, such as BTC®1010, BTC®818 available from Stepan Company Northfield, Ill.; alkyl dimethyl benzyl ammonium chloride (ABDAC); dialkyldimethyl ammonium chloride (DDAC); n-alkyl dimethyl benzyl ammonium chloride; alkyl dimethyl benzyl ammonium saccharinate; and combinations thereof. For example, ABDAC and DDAC can be combined in any suitable ratio to comprise the quat, for example, about 60%/40% DDAC/ADBAC, alternatively about 50%/50%, about 55%/45%, about 45%/55%, about 40%/60%, about 65%/35%, about 35%/65%, about 30%/70%, about 70%/30%, about 25%/75%, about 75%/25%, about 80%/20%, about 20%/80% DDAC/ADBAC, or any combination therebetween. Additional suitable quats can be obtained from Stepan Company, Northfield Ill., for example, BTC®835, BTC®824, BTC®1010, BTC®1210, BTC®885, BTC®1210-80%, BTC®2125M, BTC®471M, or any combination thereof.

The presently described technology and its advantages will be better understood by reference to the following examples. These examples are provided to describe specific embodiments of the present technology. By providing these specific examples, it is not intended to limit the scope and spirit of the present technology. It will be understood by those skilled in the art that the full scope of the presently described technology encompasses the subject matter defined by the claims appending this specification, and any alterations, modifications, or equivalents of those claims.

EXAMPLES

The compositions and processes described here, and ways to make and use them are illustrated by the following examples. Examples stated in the present or future tense are not represented as having been carried out. Examples demonstrating how sulfonated estolides have been prepared and used were previously been described in detail in PCT Application Serial No. PCT/US09/31608 filed on Jan. 21, 2009 which is hereby incorporated by reference in its entirety including all examples.

Example 1

Preparation of SE Sulfonic Acid

The fatty acid feedstock used was derived from a vegetable oil source. For the purpose of sulfonation, the feedstock had an equivalent weight of about 270.6, as determined by iodine value. The feedstock was comprised of about 80% C-18:1, about 12.5% C-18:2, and about 7.5% saturated fatty acids, as measured by area count data obtained by gas chromatography using a flame ionization detector.

The feedstock was sulfonated on a falling film reactor using a feedstock temperature of about 15° C., an air/$SO_3$ temperature of about 40° C., a sulfonator jacket temperature of about 42° C., and a molar ratio of $SO_3$ to alkene functionality of about 1.0. After passing through a degassing unit, the acid produced from the sulfonation reaction was collected in small glass jars, frozen in an ice bath, and then stored in a freezer until further processing.

Analysis of Acid: The carboxylic acid content in the SE sulfonic acid product was determined by dissolving an aliquot of product in water that contained sufficient KOH to afford a solution with a pH greater than about 10.5. Titration of the solution with aqueous HCl indicated a free carboxylate content of about 2.04 milliequivalents per gram of sulfonated acid (meq/g). The sulfonic acid product was analyzed for carboxylic ester content by subjecting an aliquot of the acid to exhaustive alkaline hydrolysis conditions and then analyzing for carboxylate content. To accomplish this hydrolysis, an aliquot of product that was dissolved in dilute aqueous KOH was then digested for about 16 hours in an 85° C. oven, ensuring that the pH of the solution remained above about 10.5, and was then titrated with aqueous HCl. The carboxylate content, on the basis of starting sulfonic acid product mass, was thereby determined to be about 3.18 meq/g. The change in carboxylate content upon hydrolysis is attributable to the hydrolysis of carboxylic esters. Therefore, the amount of carboxylic ester functionality was found to be about 36 mol percent of the total carboxylic functionality (carboxylic acid+carboxylic ester) present in the SE sulfonic acid product. $^1$H and $^{13}$C NMR spectra of the acid product dissolved in CDCl$_3$ displayed signals that were consistent with the structure of alpha-sulfo-estolide functionality. In addition, $^1$H NMR spectral data indicated that the SE sulfonic acid composition was further comprised of approximately 10 mol % of internal gamma sultones (1,3 dialkyl 1,3 sultones) relative to the total carboxylic functionality (carboxylic acid+ester).

Example 2

Comparison of Surface Activities

The surface activities of SE were compared with other commonly used anionic surfactants, STEOL® CS-230 (Sodium Laureth Sulfate, 2EO), STEOL® CS-330 (Sodium Laureth Sulfate, 3EO), STEPANOL® WA-EXTRA (Sodium Lauryl Sulfate), all available from Stepan Company, Northfield, Ill. The surface activity was measured using a Kruss K12 tensiometer at 25° C. in deionized water. The results can be found in Table 1 below. The critical micelle concentration (CMC) and the surface tension at CMC are important properties for a surfactant. CMC indicates the minimum concentration of a surfactant that forms aggregates. The surfactant with a lower CMC is believed to be more effective to emulsify or remove oil than a surfactant with a higher CMC. The surface tension indicates how efficient a surfactant can reduce the surface energy of water. Lower surface tension is favorable for wetting and cleansing. The results showed that SE is an improved and effective surfactant in terms of CMC and surface tension characteristics.

TABLE 1

|  | CMC (mg/L) | Surface Tension @CMC (mN/m) |
| --- | --- | --- |
| SE | 36.1 | 34.5 |
| STEPANOL WA-EXTRA (SLS) | 184.8 | 26.3 |
| STEOL CS-230 (SLES-2) | 171 | 25 |
| STEOL CS-330 (SLES-3) | 75 | 30 |

Example 3

Coupling Ability of SE with Nonionic Surfactants of Different HLB

Sodium xylene sulfonate (SXS) is often used as a hydrotrope to clarify cloudy formulations. However, SXS is not a surfactant and does not add to the cleaning power of the formulation. SE can be used as a cleaning active and a hydrotrope to clarify a cloudy nonionic blend. Sodium linear alkyl benzene sulfonate (NaLAS) is a common surfactant used in cleaning formulations and it was not able to clarify the formulation. In Table 2, the measurement of the amount of hydrotrope or surfactant needed to clear the solution was determined.

TABLE 2

| Formula | SE % actives | with SXS % actives | with LAS % actives |
|---|---|---|---|
| Bio-soft N25-9 (HLB 13) | 5 | 5 | 5 |
| Bio-Soft N25-3 (HLB 8) | 5 | 5 | 5 |
| trisodium citrate•2H$_2$O | 1 | 1 | 1 |
| hydrotrope requirement (actives) | 6.2 | 5.3 | 8.3 |
| Final appearance | clear solution | clear solution | did not clear, just got thicker |

The compositions described in Table 2 are made in accordance with the following steps:
Add the water and trisodium citrate and mix until the solution is clear. Add BIO-SOFT® N25-9 slowly until the solution is homogeneous. Add BIO-SOFT® N25-3 and mix until the solution is homogeneous. If the final solution is cloudy, then continue adding the hydrotrope or surfactant and agitate until solution is clear. As can be seen from Table 2, SE is an effective clarifier.

Example 4

SE in Hard Surface Cleaner Concentrate and as a Fragrance Solubilizer

SE is a sulfonated estolide and was tested as a fragrance stabilizer as described in the following compositions in Table 3 where the pH was adjusted accordingly:

TABLE 3

| ingredient | wt % | wt % | wt % | wt % |
|---|---|---|---|---|
| sodium lauryl sulfate (30% actives) | 26.7 | | | |
| SE (53% actives) | | 15.09 | 15.09 | 15.09 |
| Hydrophobic orange fragrance | 1.5 | 1.5 | 1.50 | 1.50 |
| 5% H2SO4 | | | 5.00 | |
| adjust with NaOH | | | | q.s. |
| Deionized water | balance | balance | balance | balance |
| pH | 7-8 | 7-8 | 3-4 | 10-11 |
| appearance | cloudy | cloudy | clear | cloudy | sodium lauryl sulfate is not stable at pH 3-4
All ingredients in Table 3 were on a % wt as is basis.

As can be seen from Table 3, SE can solubilize the fragrance at the low pH, but not at the higher pH. At the lower pH, the SE is thought to have more fatty acid end groups instead of carboxylates, which is thought to act as a good stabilizer of fragrances. One of the benefits of the SE and HSE is that the surfactant properties can be manipulated by changing the pH. Additionally, as a result, this formulation can be used a dilutable concentrate or used on a wipe. Further, it should be appreciated that an essential oil or natural fragrance can be substituted for the hydrophobic orange fragrance in the example in Table 3 and replace the H2SO4 with a natural acid such as glycolic, lactic or citric acid or combinations thereof to result in an all-natural formula.

In some cases essential oils can be used as an antimicrobial or disinfecting agent. One prophetic example of an antimicrobial or disinfecting composition of the present technology is set forth in Table 4. It is contemplated that the pH of the composition set forth in Table 4 will be adjusted using a carboxylate chelating agent made from a natural source like malonic acid, aspartic acid, glutamic acid, citric acid, glycolic acid, lactic acid or a combination thereof to make an all-natural formulation. Alternatively, for a non-natural formulation, sulfuric acid or some other like acid is contemplated to be used to adjust the pH.

TABLE 4

| | % Wt | % Wt | % Wt |
|---|---|---|---|
| Thyme oil | 0.4 | | |
| Clove oil | | 0.1 | |
| Geranium oil | 0.2 | | |
| Geraniol | | 0.1 | 0.5 |
| Eucalyptus oil | | 0.2 | 0.2 |
| SE and/or HSE | 3.0 | 0.5 | 10.0 |
| Diethylene triamine penta methylene phosphonate | 0.15 | 0.2 | 0.15 |
| water and minors | to 100% | to 100% | to 100% |

All ingredients in Table 4 are as is except surfactants are on an active basis.

Additional antimicrobial and disinfecting examples can be found within U.S. Pat. No. 6,048,836 and are hereby incorporated by reference.

Table 5 is a formulation of a floor cleaner concentrate of at least one embodiment of the present technology. It may be used as a ready to use product or diluted to about 1 to about 2 oz in a gallon of a delivery vehicle (for example, water) according to Table 5 for cleaning of hard surfaces. The illustrative composition set forth in Table 5 may exhibit antimicrobial or disinfecting properties due to the presence and amount of pine oil. The formulation of the composition set forth in Table 5 can also be adjusted with an acidic buffer, for example, a strong mineral acid, to decrease the pH within the range of about 2 to about 4.

TABLE 5

| Ingredient | wt % | wt % |
|---|---|---|
| water | 79.5 | 89.5 |
| NaOH (50%) | 0.5 | 0.5 |
| Bio-Soft S-101 | 2 | 2 |
| SE | 6 | 6 |
| alcohol ethoxylate | 1 | 1 |
| Pine Oil | 9 | 0 |
| IPA | 2 | 1 |
| fragrance | 0 | 2 |

Table 6 is a formulation of a ready to use (RTU) spray hard surface cleaner for kitchen or bathroom use. The tetrasodium ethylenediaminetetraacetic acid is used as a chelating agent and the monoethanolamine is used as an alkaline buffer.

TABLE 6

| Ingredient | active wt % |
|---|---|
| Water | to 100% |
| Tetrasodium ethylenediaminetetraacetic acid | 0.150 |
| Glycol Ether | 1.000 |
| Monoethanolamine | 0.500 |
| Alkyl amine oxide | 1.000 |
| SE | 1.000 |
| Fragrance | 0.050 |

Example 5

Sulfonated Estolide Compositions for General Cleaning Applications

At least one formulation of the present technology was tested as a general cleaner and for stability as set forth in Table 7. This general purpose cleaner can be diluted 1:4 by the cleaning person at the use site or made as a diluted product and be sold as a ready to use (RTU) product.

TABLE 7

| Ingredient[1,2] | A Control Wt % | B SE in place of AE/SLS Wt % | C HSE in place of AE/SLS Wt % | D SE in place of DB Wt % | E HSE in place of DB Wt % | F SE in place of PnB Wt % | G HSE in place of PnB Wt % |
|---|---|---|---|---|---|---|---|
| C1214 EO-8 | 0.90 | — | — | 0.90 | 0.90 | 0.90 | 0.90 |
| Sodium lauryl sulfate (SLS) | 0.3 | — | — | 0.3 | 0.3 | 0.3 | 0.3 |
| SE | — | 1.2 | — | 4.0 | — | 4.0 | — |
| HSE | — | — | 1.2 | — | 4.0 | — | 4.0 |
| Diethylene glycol monobutyl ether | 4.0 | 4.0 | 4.0 | — | — | 4.0 | 4.0 |
| Propylene glycol n-butyl ether | 4.0 | 4.0 | 4.0 | 4.0 | 4.0 | — | — |
| Sodium Citrate | 4.0 | 4.0 | 4.0 | 4.0 | 4.0 | 4.0 | 4.0 |

[1]All ingredients were as is except surfactants are on an active basis
[2]After adding all formulation ingredients including optional additives, water was used to bring the total weight to 100%.

The sulfonated estolide SE sample used in this example was produced from 100% oleic acid feed stock. The final product was the result of neutralization, hydrolysis, and bleaching (using approximately 1.1% by weight of about 50% H2O2 per acid flow). The final product consisted of approximately 71.37% solids at a pH of about 5.02 with a % K2SO4 of about 2.41. The formulation had a pH range of about 6.5 to about 8.5.

Example 6

General Purpose Kitchen Cleaner Performance

SE and HSE are sulfonated estolide compositions of general Formula 1, preparation of which is partially described in Example 1, and which can structurally be described within the constructs of Formula 1. Both SE and HSE can unexpectantly and unpredictably replace both the anionic and nonionic surfactants without losing soil removal performance and without detrimental foaming, and with equal or better filming and streaking performance as demonstrated by Table 8. The composition evaluated in this assay is described in Example 5 and Table 7.

SE and HSE were evaluated by ASTM 4488 section A5 for % soil removal to determine the cleaning effectiveness of the formulations, and tested by a filming and streaking method to determine effectiveness as hard surface cleaners. The formulas were diluted 1:4 with deionized water before the tests were performed. The methodology for the filming and streaking assay is as follows:

(1) Black tiles or mirrored tiles are cleaned with a standard spray and wipe glass cleaner. The tile was then rinsed with isopropyl alcohol and allowed to dry.

(2) Ten drops of the hard surface cleaner sample were evenly applied around the hard surface material. The drops should be applied in a uniform pattern, size and shape on the hard tile surface.

(3) The treated tile is wiped with a quartered tissue which has been folded in half. The tissue is wiped across the tile's surface for ten cycles while applying light and uniform pressure. One cycle is equal to one back and forth motion.

(4) The hard surfaces are dried for a minimum of ten minutes.

(5) The hard surfaces are then visually evaluated and scored under well lighted conditions. The scoring of the streaking and filming performance is conducted using a plus or minus rating scale, where the control is set to zero and a positive score is indicative of superior performance.

TABLE 8

|  | A Control | B SE in place of AE/SLS | C HSE in place of AE/SLS | D SE in place of DB | E HSE in place of DB | F SE in place of PnB | G HSE in place of PnB |
|---|---|---|---|---|---|---|---|
| % soil removed | 84.5 | 81.7 | 92.1 | 81.9 | 88.1 | 82.6 | 96.7 |
| Filming | 0 | +1 | = | −1/= | =/+1 | = | =/+1 |
| Streaking | 0 | +1 | +1 | = | = | = | = |

A difference of 10% soil removal shows the formulas performed differently. For the filming and streaking test, the control's performance is set as 0. Positive (greater than zero) results show improved performance.

Unexpectedly, it was observed that SE can replace either solvent and yet appeared to maintain soil removal performance. In replacing diethylene glycol monobutyl ether, it might leave more of a film, but is equal in streaking performance. In replacing propylene glycol n-butyl ether, SE maintains the filming and streaking performance.

SE can replace diethylene glycol butyl ether and maintain cleaning performance while maintaining or improving the filming and streaking performance. In replacing propylene glycol n-butyl ether, HSE improves the soil removal without decreasing streaking, while maintaining or improveing filming.

Usually two surfactants are needed to achieve cleaning and to keep filming and streaking to an acceptable level. Most hard surface cleaners need a nonionic surfactant to provide the proper wetting and cleaning and an anionic surfactant to decrease the filming and streaking. As demonstrated by Columns B and C of Table 8, SE and HSE are able to do the job of both the anionic and nonionic surfactants.

Historically, a combination of solvents is used to aid in cleaning to improve the filming and streaking performance by controlling the evaporation rate. It was unexpected that replacing a solvent with a surfactant, as described in Formula 1, could maintain or improve the performance. However, as demonstrated by Columns D, E, F and G, SE and HSE can replace one solvent and still have the same or better filming and streaking performance.

Further testing was conducted to determine whether SE or HSE could replace solvents found in traditional hard surface cleaning formulations. The composition set forth in Table 9 is intended to be diluted 1:4 in water before its final use by the consumer.

TABLE 9

| Ingredient[1] | A<br>Control<br>Wt % | B<br>SE in place of<br>both solvents<br>Wt % | C<br>HSE in place of both<br>solvents<br>Wt % |
|---|---|---|---|
| C1214 EO-8 | 0.90 | 0.9 | 0.9 |
| Sodium lauryl sulfate | 0.3 | 0.3 | 0.3 |
| SE | — | 8.0 | — |
| HSE | — | — | 8.0 |
| Diethylene glycol monobutyl ether | 4.0 | — | — |
| Propylene glycol n-butyl ether | 4.0 | — | — |
| Sodium Citrate | 4.0 | 4.0 | 4.0 |
| Sulfuric acid | | | qs |
| Deionized water | balance | balance | balance |
| pH | 7.4 | 7.3 | 6.0 |
| appearance | clear | clear | clear |

[1]All ingredients are as is except surfactants are on an active basis.

TABLE 10

| | A<br>Control | B<br>SE in place of<br>both solvents | C<br>HSE in place of both<br>solvents |
|---|---|---|---|
| % soil removed | 72 | 61 | 74 |
| Filming | 0 | = | +1 |
| Streaking | 0 | +1 | +2 |

A difference of 10% soil removal shows the formulas performed differently. For the filming and streaking test, the control's performance is set as 0. Positive (greater than zero) results show improved performance.

Table 10 illustrates the unexpected and unpredictable results outcome in which SE and HSE can replace both solvents (diethylene glycol monobutyl ether and propylene glycol n-butyl ether) in a hard surface cleaning performance assay. Although the cleaning performance is decreased in the SE experimental group, the HSE showed equivalent cleaning to the control. Both SE and HSE showed an improved filming and streaking profile when compared to control. The formulas B and C above can be made into all natural formulas by replacing the alcohol ethoxylate (C1214 EO-8) with a surfactant such as coconut alkyl polyglucoside or $C_{8-10}$ alkyl polyglucoside made from natural raw materials. If an acid adjustment is needed for formula C, then a natural acid can be used.

Example 7

Improved Formulation Stability

In order to have a commercially viable product, the composition is required to be stable such that the consumer or professional cleaning company will purchase active product when brought home and utilized. To establish the stability of the present technology, a high temperature stability assay was employed where the composition was evaluated at 50° C. The high temperature stability assay is also intended to mimic an accelerated ambient temperature environment. Table 11 sets forth the results of the high temperature stability experimentation. The composition of the materials in Table 11 can be found in Table 7.

TABLE 11

| Assay Temp. | | A<br>Control | B<br>SE in place<br>of AE/SLS | C<br>HSE in<br>place of<br>AE/SLS | D<br>SE in<br>place of<br>DB | E<br>HSE in<br>place of<br>DB | F<br>SE in<br>place of<br>PnB | G<br>HSE in place<br>of PnB |
|---|---|---|---|---|---|---|---|---|
| 50° C. | 1 day | Pass | Pass | Pass | Pass | Pass | Pass | Pass |
| | 1 week | Pass | Pass | Pass | Pass | Pass | Pass | Pass |
| | 2 weeks | Pass | Pass | Pass | Pass | Pass | Pass | Pass |
| | 3 weeks | Fail | Pass | Pass | Pass | Pass | Pass | Pass |
| | 1 month | Fail | Pass | Pass | Pass | Pass | Pass | Pass |

As can be seen in Table 11, SE and HSE demonstrated superior stability compared to the control when evaluated for long-term stability (via the accelerated ambient temperature assay) as well as stability in high temperatures. In the accelerated ambient temperature assay, the control failed stability tests at 3 to 4 weeks, whereas the SE and HSE formulas were still stable. This is a surprising and unpredictable outcome.

Example 8

Improved Stability of Concentrated Formulation

A growing trend in the cleaning industry is the concept of concentrated formulas. The retailers and manufacturers have an economic interest in concentrated formulations due to transit costs, storage fees and shelf-space considerations. These sulfonated estolide (SE/HSE) formulations can be concentrated.

Table 12 demonstrates the stability of concentrated formulations of sulfonated estolide compositions. The formulations of Table 12 have been concentrated to 8x; therefore, the end consumer would be expected to dilute the formulation in a 1:8 ratio with water before use. Not all sulfonated estolide compositions can be concentrated. Although not wanting to be bound by any particular theory, it is believed based upon the testing provided herein (see, e.g. Table 12 below) that hydrolyzed (HSE) samples appear to concentrate more easily than non-hydrolyzed (SE) samples.

TABLE 12

|  |  | Control | SE in place of AE/SLS | HSE in place of AE/SLS | SE in place of DB | HSE in place of DB | SE in place of PnB | HSE in place of PnB |
|---|---|---|---|---|---|---|---|---|
| 50° C. | 1 day | Not soluble | Not soluble | Pass | Not soluble | Pass | Pass | Pass |
| High temperature stability | 1 week | NA | NA | Pass | NA | Pass | Pass | Pass |
|  | 2 weeks |  |  | Pass |  | Pass | Pass | Pass |
|  | 3 weeks |  |  | Pass |  | Pass | Pass | Pass |
|  | 1 month |  |  | Pass |  | Pass | Pass | Pass |

NA = not applicable

The stability results above demonstrate that concentrated formulations of the present technology can be manufactured and shipped to the point of consumer sale while maintaining an active and stable hard surface cleaning composition. This is advantageous and unexpected in comparison to conventional concentrated compositions which often contain ingredients that are less environmentally friendly; have higher volatile organic carbons (VOC), may be sensitizers; or cannot be concentrated to the same degree as the sulfonated estolide formulation of the present technology.

Example 9

Degreaser Application

One or more sulfonated estolide formulations of the present technology were evaluated as an application for degreasing at a pH of greater than about 12. Most effective degreasing formulations have a pH of about 9 or greater. This formula could have a lower pH of about 10.5 if the sodium metasilicate was removed as a co-adjuvant. For "green" or eco-friendly formulations a pH of less than 11.5 is preferred. Due to the alkaline environment, only hydrolyzed SE (i.e., HSE) could be tested. Table 13 sets forth the compositions of the degreaser formulations tested. The formulations set forth in Table 13 are expected to be diluted 1:8 in water by the end consumer before use.

TABLE 13

| Ingredient[1,2,3] | Control Wt % | HSE in place of sodium octane sulfonate Wt % | HSE in place of both AE Wt % | HSE in place of all surfactants Wt % | HSE in place of DB Wt % |
|---|---|---|---|---|---|
| Sodium octane sulfonate | 3.8 | — | 3.8 | — | 3.8 |
| C11 EO7, alcohol ethoxylate (AE, nonionic) | 1.0 | 1.0 | — | — | 1.0 |
| C9-11 EO6 alcohol ethoxylate (AE, nonionic) | 1.0 | 1.0 | — | — | 3.0 |
| HSE | — | 3.8 | 2.0 | 5.8 | 3.0 |
| Diethylene glycol monobutyl ether (DB) | 3.0 | 3.0 | 3.0 | 3.0 | — |
| Dipropylene glycol n-butyl ether | 3.0 | 3.0 | 3.0 | 3.0 | 3.0 |

TABLE 13-continued

| Ingredient[1,2,3] | Control Wt % | HSE in place of sodium octane sulfonate Wt % | HSE in place of both AE Wt % | HSE in place of all surfactants Wt % | HSE in place of DB Wt % |
|---|---|---|---|---|---|
| Sodium metasilicate | 1.0 | 1.0 | 1.0 | 1.0 | 1.0 |
| Sodium carbonate | 1.0 | 1.0 | 1.0 | 1.0 | 1.0 |

[1]All solutions were free of visible precipitates.
[2]All ingredients were "as is" except surfactants are on an "active" basis.
[3]After adding all formulation ingredients including optional additives, water was used to bring the total weight to 100%.

The sulfonated estolide composition of Table 13 was diluted 1:8 in deionized water for performance testing. A dilution of less than 1:8 can be used for heavy-duty degreasing applications. The results of the degreasing performance are set forth in Table 14.

TABLE 14

|  | Control | HSE in place of sodium octane sulfonate | HSE in place of both AE | HSE in place all surfactants | HSE in place of DB |
|---|---|---|---|---|---|
| % soil removed | 57.3 | 74.5 | 55.3 | 81.4 | 56.6 |
| filming | 0 | = | = | = | = |
| streaking | 0 | = | = | =/+1 | = |

A difference of 10% soil removal shows the formulas to perform differently. For the filming and streaking test, the control's performance is set as 0.

It was surprisingly and unexpectedly found from the testing as illustrated in Tables 13 and 14 that HSE components of the present technology can replace the anionic surfactant, which is a hydrotropic surfactant, and significantly improve the cleaning performance, while the filming and streaking performances remain similar to conventional degreaser formulations not containing the HSE component. Thus, it is significant and unpredictable in the degreaser formulations that replacement of only the nonionic surfactants can be done without decreasing performance. Most hard surface cleaners need a nonionic surfactant to provide the proper wetting and cleaning and an anionic surfactant to decrease the filming and streaking. The replacement of both the nonionic and anionic, while increasing the cleaning performance and showing equal or better filming and streaking performance is excellent via the formulations of the present technology.

When HSE replaced the diethylene glycol monobutyl ether solvent as indicated also in Table 13, results demonstrate that HSE had equal cleaning and streaking performance, yet without the negative environmental impact. Diethylene glycol monobutyl ether is a solvent considered to be a hazardous air pollutant, whereas HSE is a biodegradable surfactant. It is therefore significant that the experimental results demonstrate that a hazardous air pollutant can be replaced with a biodegradable surfactant without sacrificing cleaning performance. Dipropylene glycol n-butyl ether was present in the performance testing formulation. However, it is notable that dipropylene glycol n-butyl ether is not a hazardous air pollutant or a volatile organic compound. These results further demonstrate that use of sulfonated estolides in hard surface cleaning applications can quite surprisingly lead to a consumer product with equal or better cleaning performance compared to traditional cleaners, and a "greener" or more "eco-friendly" formulation with less of an environmental impact.

Example 10

Acid Bathroom Spray Cleaner

The composition set forth in Table 15 would be appropriate for a ready-to-use formulation. Testing was conducted to determine whether SE and HSE could be used as an acidic pH bathroom cleaner. The low pH and the surfactants combine to form a descaling composition which removes soap scum and hard water deposits.

TABLE 15

|  | Control wt % | SE in place of surfactant wt % | SE in place of DB wt % | HSE in place of DB wt % |
|---|---|---|---|---|
| alcohol ethoxylate C911 EO 6 | 1.0 | — | 1.0 | 1.0 |
| SE | — | 1.0 | 2.0 | — |
| HSE | — | — | — | 2.0 |
| propylene glycol n-butyl ether | 1.0 | 1.0 | 1.0 | 1.0 |
| diethylene glycol butyl ether (DB) | 2.0 | 2.0 | — | — |
| Citric Acid | 5.0 | 5.0 | 5.0 | 5.0 |
| Deionized Water | balance | balance | balance | balance |
| pH | 2.4 | 2.4 | 2.8 | 2.6 |
| High Temperature Stability (50 C.) | | | | |
| 1 day | Pass | Pass | Pass | Pass |
| 1 week | Pass | Pass | Pass | Pass |
| 2 week | Pass | Pass | Pass | Pass |
| 3 week | Fail | Pass | Pass | Pass |
| 1 month | NA | Pass | Pass | Pass |

The results above demonstrate that SE can be used in place of the nonionic surfactant and both SE and HSE can be used to replace the DB solvent. The formulas with the SE and HSE have improved high temperature stability relative to the control sample.

Example 11

Lime Soap Dispersing Application

Additional testing was conducted to determine the effectiveness of the sulfonated estolide formulation of the present technology as a lime soap dispersing agent. Table 16 sets forth the results of the lime soap dispersing experimentation, specifically, the ability of the sulfonated estolide formulation of the present technology to remove soap scum typically found in the bathroom. The test solutions reported in Table 16 were made of each surfactant at 0.5% activity. A 0.5% sodium oleate solution was made. A 1000 ppm hard water solution was made.

5 g of the sodium oleate solution was added to an empty vial. The various amounts of test solution were added next. An amount of deionized water was added such that the amount of test solution and water added to 15 g. Next 10 g of the hard water was added. The vial was sealed and inverted 20 times. The sample was allowed to sit for 30 seconds and then was observed. If the solutions were clear or translucent, then the soap was considered dispersed. Subsequent lower levels of the test solution are used until the product fails to disperse the soap. A failure is reached when solid clumps are seen in the solution. Solutions were tested to give results in 10% increments. The lowest amount of test solution used that was able to disperse the soap, was the weight used in the formulation below. The lime soap dispersing percentage was calculated by the following formula:

100(0.5% active surfactant solution)(wt. of test solution used)/(0.025 g sodium oleate).

Historically, methyl ester sulfonates have demonstrated the ability to disperse lime soap, therefore, two methyl ester sulfonates were used as positive controls. The experimental protocol is such whereby a lower lime soap dispersing power percentage translates into a more effective lime soap dispersing agent.

TABLE 16

| surfactant | Lime soap dispersing power |
|---|---|
| SE | 40% |
| HSE | >100% |
| Stripped coco methyl ester sulfonate, Na salt | 80% |
| C1618 methyl ester sulfonate, Na salt | 30% |

The methodology employed in this lime soap dispersing assay can be found in an article in JAOCS 42:805-810 (1965) (the "Borghetty and Bergman method") as described at the fall meeting of the American Oil Chemist' Society, Chicago, Oct. 31, 1949.

As demonstrated by Table 16, sulfonated estolide formulations of the present technology exhibited lime soap dispersing efficacy on par with historically known lime soap dispersing agents.

Example 12

Toilet Bowl Composition

Manual toilet bowl cleaner formulations are most effective at an acidic pH because such a pH enables the composition to remove hard water and rust stains from the toilet bowl. Toilet bowl cleaner formulations are usually made at a high viscosity to prevent splashing and to prolong contact with the surface to be cleaned. All components in this contemplated formula are made from biorenewable materials, including SE and HSE which makes this an all natural formulation.

TABLE 17

| Ingedients | Control | With SE | With HSE |
|---|---|---|---|
| Alkyl polyglucoside | 2.75 | | |
| SE | | 2.75 | |
| HSE | | | 2.75 |
| Citric acid | 5.0 | 5.0 | 5.0 |
| Xanthan gum | 0.6 | 0.75 | 0.7 |
| Deionized water | balance | balance | balance |
| pH | 2.3 | 2.6 | 2.8 |
| appearance | Clear, viscous liquid/gel | Clear, viscous liquid/gel | Opaque, viscous liquid/gel |
| Viscosity, cps | 500 | 270 | 390 |

All components in this formula are made from biorenewable materials and values represent percent weight of total composition, except for the surfactant values which represent percent weight of actives.

Example 13

Additional Formulations

The following formulations are contemplated to be useful formulations for SE, as well as HSE and PHSE with an appropriate substitution.

TABLE 18

| | Carpet Cleaner | | | |
|---|---|---|---|---|
| | Example 1 | | Example 2 | |
| Component | (%) actives | (%) actives | (%) actives | (%) actives |
| Tetrapotassium pyrophosphate | 0 to 7 | 4 | 0 to 7 | 4 |

TABLE 18-continued

| | Carpet Cleaner | | | |
|---|---|---|---|---|
| | Example 1 | | Example 2 | |
| Component | (%) actives | (%) actives | (%) actives | (%) actives |
| STEPOSOL ® DG | 0 to 7 | 4 | 0 to 7 | 4 |
| 1-methoxy-2-propanol | 0 to 7 | 4 | 0 to 7 | 4 |
| BIO-TERGE ® PAS 8S | 1 to 10 | 6 | | |
| SE | | | 1 to 10 | 6 |
| Tetrasodium etilenediaminetetraacetate | 0 to 5 | 2 | 0 to 5 | 2 |
| Fragrance, dye, preservative | 0 to 1 | 0.3 | 0 to 1 | 0.3 |
| Water | Up to 100 | Up to 100 | Up to 100 | Up to 100 |

TABLE 19

| | Antimicrobial. Ready to Use. Formula | |
|---|---|---|
| Ingredient | (%) actives | (%) actives |
| DI Water | Up to 100 | Up to 100 |
| SE | 0 to 10 | 4.00 |
| C1215 Alcohol ethoxylate 7 mol | 0 to 10 | 4.00 |
| Alkyl dimethyl benzyl ammonium chloride and ethyl benzyl chloride | 0.01 to 0.15 | 0.005 |
| Sodium carbonate anhydrous | 0 to 10 | 1.00 |
| Tetrasodium ethylenediaminetetracetate | 0 to 5 | 0.40 |
| Ethylene glycol monobutyl ether | 0 to 10 | 2.00 |
| Fragrance, dye | 0 to 2 | 0.30 |

The embodiments and examples described herein are illustrative, and do not limit the presently described technology in any way. The scope of the present technology described in this specification is the full scope defined or implied by the claims. Additionally, any references noted in the detailed description section of the instant application are hereby incorporated by reference in their entireties, unless otherwise noted

What is claimed is:

1. A surfactant composition, comprising:
about 0.1% to about 99% by weight of at least one surfactant having the following general Formula 1:

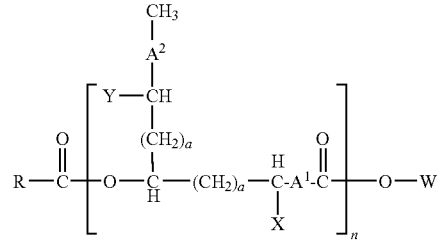

Formula 1 wherein n is an integer from 1-30, or mixtures thereof;
one of X and Y is $SO_3$—Z, the other of X and Y is H, and X and Y are independently assigned in each repeating unit;
$A^1$ and $A^2$ are linear or branched, saturated or unsaturated, substituted or unsubstituted, alkyl diradicals wherein the total number of carbons for each repeating unit is independent and in the range of $C_8$ to $C_{22}$;

a is 0, 1, or 2, and is independently assigned in each repeating unit;

R is linear or branched, saturated or unsaturated, substituted or unsubstituted hydrocarbon wherein the total number of carbon atoms is from 1 to 24;

W is H or a monovalent or divalent metal cation, ammonium cation, substituted ammonium cation, or an alkyl or substituted alkyl group; and Z is H or a monovalent or divalent metal cation, ammonium or substituted ammonium cation;

about 0.1% to about 99% of at least one carrier; and about 0.1% to about 50% weight of at least one solvent based upon the total weight of the composition;

wherein the composition is a hard surface or substrate cleaner;

wherein the solvent is selected from the group consisting $C_1$-$C_8$ alcohols, glycol ethers, ketones, ethylene glycol, hexylene glycol, alkyl lactyl lactates, d-limonene, pine oil, essential oils, sorbitol, 1,3-propane diol, tertiary alcohols of up to 8 carbon atoms, aromatic-substituted alcohols, polyalkylene glycols having up to 6 carbon atoms per alkylene group, mono- or dialkyl ethers of alkylene glycols or poly-alkylene glycols having up to 6 carbon atoms per glycol group and up to 6 carbon atoms in each alkyl group, mono- or diesters of alkylene glycols or polyalkylene glycols having up to 6 carbon atoms per glycol group and up to 6 carbon atoms in each ester group, combinations thereof and derivatives thereof.

2. The composition of claim 1, wherein the hard surface or substrate cleaner is a member selected from the group consisting of a degreaser, a descaler, a bathroom cleaner, a toilet bowl cleaner, a glass cleaner, a floor cleaner, a carpet cleaner, a biocidal cleaner, and an all-purpose general cleaner.

3. The composition of claim 1, wherein the composition further comprises at least one acidic buffer, or at least one alkaline buffer, or combinations thereof to adjust the pH of the composition.

4. The composition of claim 3, wherein the at least one acidic buffer is derived from a natural or synthetic source and comprises from about 0.1% to about 10% by weight based upon the total weight of the composition.

5. The composition of claim 4, wherein the natural acidic buffer is a member selected from the group consisting of mineral acids and 2-hydroxycarboxylic acids, derivatives thereof, and combinations thereof.

6. The composition of claim 4, wherein the synthetic acidic buffer is a member selected from the group consisting of oxalic acid, lactic acid, sulfamic acid, valeric acid, hexanoic acid, glycolic acid, formic acid, acetic acid, propionic acid, butyric acid, gluconic acid, acetic acid, peroxyacetic acid, derivatives thereof, and combinations thereof.

7. The composition of claim 3, wherein the at least one alkaline buffer is derived from a natural or synthetic source and comprises from about 0.1% to about 15% by weight based upon the total weight of the composition.

8. The composition of claim 7, wherein the natural alkaline buffer is a member selected from the group consisting of alkali metal carbonate, alkali metal bicarbonate, alkaline earth metal hydroxide, alkali metal and alkaline earth salts of silicates, borate, ammonium hydroxide, derivatives thereof, and combinations thereof.

9. The composition of claim 7, wherein the synthetic alkaline buffer is a member selected from the group consisting of alkanolamines, ammonium carbonate, ammonium bicarbonate, ethylenediaminetetraacetic acid, trialkyl salts of nitrilotriacetic acid, phosphates, derivatives thereof, and combinations thereof.

10. The composition of claim 1, wherein the composition exhibits a pH from about 2 to about 13.

11. The composition of claim 1, wherein the composition further includes at least one additive which comprises from about 0.1% to about 10% by weight of the total weight of the composition.

12. The composition of claim 11, wherein the at least one additive is a member selected from the group consisting of adjuvants, adjuvant/builders, buffers, viscosity modifiers, electrolytes, emollients, skin conditioning agents, emulsifiers;

suspending agents; fragrances, essential oils, colorants, herbal extracts; vitamins;

pigments; enzymes; preservatives; derivatives thereof, and combinations thereof.

13. The composition of claim 1, wherein the composition further comprises at least one additional surfactant, or mixtures thereof, which comprises about 0.1% to about 50% by weight of the composition.

14. The composition of claim 13, wherein the additional surfactant is a member selected from the group consisting of natural surfactants, synthetic surfactants, and combinations thereof.

15. The composition of claim 14, wherein the natural or synthetic surfactants is a member selected from the group consisting of anionic surfactants, cationic surfactants, ampholytic surfactants, zwitterionic surfactants, nonionic surfactants, derivatives thereof, and combinations thereof, which comprises from about 0.1% to about 50% by weight of the total weight of the additives of the composition.

16. The composition of claim 15, wherein the anionic surfactant is a member selected from the group consisting of alcohol sulfates, alkane sulfonates, alkyl ether sulfates, alkyl diphenol oxide disulfonates, alkyl ester sulfonates, and combinations thereof.

17. The composition of claim 15, wherein the nonionic surfactant is a member selected from the group consisting of alkyl polyglucosides, alkyl carboxylic acid esters, alcohol alkoxylates, alkyl phenol alkoxylates, alkyl ethanolamides, alkyl esters, derivative thereof and combinations thereof.

18. The composition of claim 15, wherein the ampholytic surfactant is a member selected from the group consisting of amine oxides, amidopropyl amine oxides, betaines, amidopropyl betaines, sulfobetaines, hydroxysultaines, amphoacetates, amphopropionates, alkyl amines, organic diamines, derivatives thereof and combinations thereof.

19. The composition of claim 15, wherein the zwitterionic surfactant is a member selected from the group consisting of betaines, imidazolines, propionates, derivatives thereof and combinations thereof.

20. The composition of claim 15, wherein the cationic surfactant is a member selected from the group consisting of alkyl trimethyl ammonium quats, alkyl dimethyl benzyl quats, alkyl amido amine quats, dialkyl amido amine quats, dialkyl dimethyl ammonium quats, mono- or di-alkyl ester quats.

21. The composition of claim 14, wherein the natural or synthetic additional surfactant comprises from about 0.1% to about 30% by weight of the total weight of the composition.

22. The composition of claim 1, wherein the solvent comprises about 0.1% to about 40% by weight of the composition based upon the total weight of the composition.

23. The composition of claim 22, wherein the solvent comprises about 0.1% to about 30% by weight of the composition based upon the total weight of the composition.

24. The composition of claim 1, wherein the composition is a clear, homogenous liquid.

25. The composition claim 24, wherein the clear, homogenous liquid exhibits phase stability.

26. The composition of claim 1, wherein the composition is substantially free of precipitation.

27. The composition of claim 1, wherein the composition is substantially free of chlorine, substantially free of phosphate or substantially free of both chlorine and phosphate.

28. The composition of claim 1, wherein the composition exhibits superior or equal cleaning performance when compared with a two or more surfactants-based cleaning composition.

29. The composition of claim 1, wherein the composition exhibits superior or equal cleaning performance when compared with a two or more solvents-based cleaning composition.

30. The composition of claim 1, wherein the composition exhibits a pH of from about 2.5 to about 6.

31. The composition of claim 1, wherein the composition exhibits a pH of from about 6 to about 13.

32. The composition of claim 1, wherein the composition exhibits a pH of from about 5 to about 10.

33. The composition of claim 1, wherein the composition can be concentrated to a concentration of about 2× to about 150×.

34. The composition of claim 1, wherein the composition can be concentrated at a concentration of about 2× to about 64×.

35. The composition of claim 1, wherein the composition can be concentrated at a concentration of about 2× to about 32×.

36. The composition of claim 1, wherein the composition exhibits a viscosity of 1 to about 2500 centipoise when measured at 25° C. using a Brookfield Viscometer Model DV-II+ having a spindle #2 and a spindle speed of about 60 rpm.

37. The composition of claim 1, wherein the composition exhibits a viscosity of 1 to about 400 centipoise when measured at 25° C. using a Brookfield Viscometer Model DV-II+ having a spindle #2 and a spindle speed of about 60 rpm.

38. The composition of claim 1, wherein the composition exhibits phase stability for a period of at least 30 days when measured in accordance with an ambient temperature stability assay.

39. The composition of claim 1, wherein the composition exhibits phase stability for a period of at least about 30 days or less when measured in accordance with a high temperature stability assay.

40. The composition of claim 1, wherein the composition further comprises a least one biocidal agent or at least one disinfecting agent in an amount of about 0.003% to about 10% by weight of the composition.

41. The composition of claim 40, wherein the biocidal agent is selected from the group consisting of ammonium quaternaries, n-alkyl dimethyl benzyl ammonium chloride; n-alkyl dimethyl ethylbenzyl ammonium chloride; dialkyl dimethyl ammonium chloride; didecyl dimethyl ammonium chloride; dioctyl dimethyl ammonium chloride; phenolics, iodophors, pine oil, methyl salicylate, morpholine, silver, copper, bromine, 1,3-dibromo-5,5-dimethylhydantoin, 1,3-dibromo-5-ethyl-5-methylhydantoin, 1,3-dibromo-5-n-propyl-5-methylhydantoin, 1,3-dibromo-5-isopropyl-5-methylhydantoin, 1,3-dibromo-5-n-butyl-5-methylhydantoin, 1,3-dibromo-5-isobutyl-5-methylhydantoin, 1,3-dibromo-5-sec-butyl-5-methylhydantoin, 1,3-dibromo-5-tert-butyl-5-methylhydantoin, derivatives thereof and mixtures thereof.

42. The composition of claim 40, wherein the biocidal agent comprises about 0.05% to about 5% by weight of the composition.

43. The composition of claim 40, wherein the disinfecting agent is selected from the group consisting of thymol, eugenol, menthol, geraniol, verbenone eucalyptol and pinocarvone, cedrol, anethol, carvacrol, hinokitiol, berberine, ferulic acid, cinnamic acid, methyl salycilic acid, methyl salycilate, terpineol, derivatives thereof and mixtures thereof.

44. A method of cleaning at least one surface or substrate, comprising the steps of:

providing a composition comprising about 0.1% to about 99% by weight of at least one surfactant having the following general Formula 1:

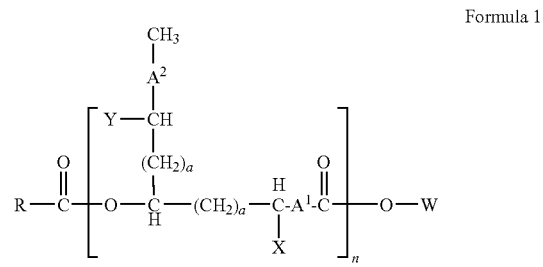

Formula 1 wherein n is an integer from 1-30, or mixtures thereof;

one of X and Y is $SO_3$—Z, the other of X and Y is H, and X and Y are independently assigned in each repeating unit;

$A^1$ and $A^2$ are linear or branched, saturated or unsaturated, substituted or unsubstituted, alkyl diradicals wherein the total number of carbons for each repeating unit is independent and in the range of $C_8$ to $C_{22}$;

a is 0, 1, or 2, and is independently assigned in each repeating unit;

R is linear or branched, saturated or unsaturated, substituted or unsubstituted hydrocarbon wherein the total number of carbon atoms is from 1 to 24;

W is H or a monovalent or divalent metal cation, ammonium cation, substituted ammonium cation, or an alkyl or substituted alkyl group; and Z is H or a monovalent or divalent metal cation, ammonium or substituted ammonium cation;

about 0.1% to about 99% of at least one carrier; and about 0.1% to about 50% weight of at least one solvent based upon the total weight of the composition;

wherein the solvent is selected from the group consisting of $C_1$-$C_8$ alcohols glycol ethers, ketones, ethylene glycol, hexylene glycol, alkyl lactyl lactates, d-limonene, pine oil, essential oils, sorbitol, 1,3-propane diol, tertiary alcohols of up to 8 carbon atoms, aromatic-substituted alcohols, polyalkylene glycols having up to 6 carbon atoms per alkylene group, mono- or dialkyl ethers of alkylene glycols or poly-alkylene glycols having up to 6 carbon atoms per glycol group and up to 6 carbon atoms in each alkyl group, mono- or diesters of alkylene glycols or polyalkylene glycols having up to 6 carbon atoms per glycol group and up to 6 carbon atoms in each ester group, combinations thereof and derivatives thereof;

contacting at least one soiled surface or substrate with the composition; and removing the composition and soil from the surface or substrate.

45. The method of claim 44, wherein the composition and soil are removed from the surface or substrate by rinsing the surface or substrate with water.

46. A glass cleaning composition, comprising:

about 0.1% to about 99% by weight of at least one surfactant having the following general Formula 1:

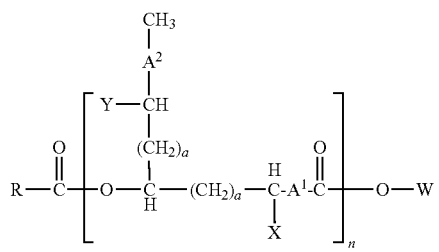

Formula 1 wherein n is an integer from 1-30, or mixtures thereof;

one of X and Y is $SO_3$—Z, the other of X and Y is H, and X and Y are independently assigned in each repeating unit;

$A^1$ and $A^2$ are linear or branched, saturated or unsaturated, substituted or unsubstituted, alkyl diradicals wherein the total number of carbons for each repeating unit is independent and in the range of $C_8$ to $C_{22}$;

a is 0, 1, or 2, and is independently assigned in each repeating unit;

R is linear or branched, saturated or unsaturated, substituted or unsubstituted hydrocarbon wherein the total number of carbon atoms is from 1 to 24;

W is H or a monovalent or divalent metal cation, ammonium cation, substituted ammonium cation, or an alkyl or substituted alkyl group; and Z is H or a monovalent or divalent metal cation, ammonium or substituted ammonium cation;

about 1% to about 3% of at least one nonionic surfactant;

about 0.5% to about 40% of at least one solvent;

optionally about 0.1% to about 5% of at least one buffer;

optionally about 0.1% to about 2% of at least one adjuvant/builder;

optionally about 0.1% to about 10% of at least one amphoteric surfactant;

optionally about 0.1% to about 1% of at least one anionic surfactant; and about 0.1% to about 99% of at least one carrier wherein the solvent is selected from the group consisting of $C_1$-$C_8$ alcohols, glycol ethers, ketones, ethylene glycol, hexylene glycol, alkyl lactyl lactates, d-limonene, pine oil, essential oils, sorbitol, 1,3-propane diol, tertiary alcohols of up to 8 carbon atoms, aromatic-substituted alcohols, polyalkylene glycols having up to 6 carbon atoms per alkylene group, mono- or dialkyl ethers of alkylene glycols or poly-alkylene glycols having up to 6 carbon atoms per glycol group and up to 6 carbon atoms in each alkyl group, mono- or diesters of alkylene glycols or polyalkylene glycols having up to 6 carbon atoms per glycol group and up to 6 carbon atoms in each ester group, combinations thereof and derivatives thereof.

47. A glass cleaning composition of claim 46, wherein the formulation can be concentrated to 20×, 40×, or 64×.

48. A bathroom cleaning composition, comprising:

about 0.1% to about 99.9% by weight of at least one surfactant having the following general Formula 1:

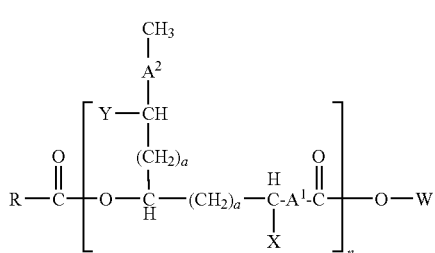

Formula 1 wherein n is an integer from 1-30, or mixtures thereof;

one of X and Y is $SO_3$—Z, the other of X and Y is H, and X and Y are independently assigned in each repeating unit;

$A^1$ and $A^2$ are linear or branched, saturated or unsaturated, substituted or unsubstituted, alkyl diradicals wherein the total number of carbons for each repeating unit is independent and in the range of $C_8$ to $C_{22}$;

a is 0, 1, or 2, and is independently assigned in each repeating unit;

R is linear or branched, saturated or unsaturated, substituted or unsubstituted hydrocarbon wherein the total number of carbon atoms is from 1 to 24;

W is H or a monovalent or divalent metal cation, ammonium cation, substituted ammonium cation, or an alkyl or substituted alkyl group; and Z is H or a monovalent or divalent metal cation, ammonium or substituted ammonium cation;

optionally about 0.1% to about 5% of at least one nonionic surfactant;

optionally about 0.5% to about 10% of at least one solvent;

optionally about 0.1% to about 10% of at least one buffer;

optionally about 0.1% to about 15% of at least one additive;

optionally about 0.1% to about 15% of at least one disinfecting agent;

optionally about 0.1% to about 2% of at least one adjuvant/builder;

optionally about 0.1% to about 2% of at least one amphoteric surfactant;

optionally about 0.1% to about 6% of at least one anionic surfactant; and about 0.1% to about 99.9% of at least one carrier wherein the composition has a pH of 5 or less.

49. A bathroom cleaning composition of claim 48, wherein the formulation can be concentrated to 10×, 20×, or 40×.

50. A floor cleaning composition, comprising:

about 0.1% to about 99% by weight of at least one surfactant having the following general Formula 1:

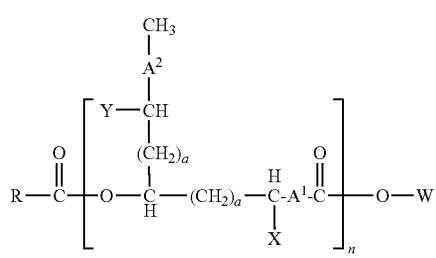

Formula 1 wherein n is an integer from 1-30, or mixtures thereof;
one of X and Y is $SO_3$—Z, the other of X and Y is H, and X and Y are independently assigned in each repeating unit;
$A^1$ and $A^2$ are linear or branched, saturated or unsaturated, substituted or unsubstituted, alkyl diradicals wherein the total number of carbons for each repeating unit is independent and in the range of $C_8$ to $C_{22}$;
a is 0, 1, or 2, and is independently assigned in each repeating unit;
R is linear or branched, saturated or unsaturated, substituted or unsubstituted hydrocarbon wherein the total number of carbon atoms is from 1 to 24;
W is H or a monovalent or divalent metal cation, ammonium cation, substituted ammonium cation, or an alkyl or substituted alkyl group; and
Z is H or a monovalent or divalent metal cation, ammonium or substituted ammonium cation;
optionally about 0.1% to about 14% of at least one nonionic surfactant;
about 0.5% to about 30% of at least one solvent;
optionally about 0.1% to about 2% of at least one buffer;
optionally about 0.1% to about 5% of at least one disinfecting agent;
optionally about 0.1% to about 5% of at least one biocidal agent;
optionally about 0.1% to about 10% of at least one amphoteric surfactant;
optionally about 0.1% to about 10% of at least one anionic surfactant;
about 0.1% to about 2% of at least one additive; and
about 0.1% to about 99% of at least one carrier
wherein the solvent is selected from the group consisting of $C_1$-$C_8$ alcohols glycol ethers, ketones, ethylene glycol, hexylene glycol, alkyl lactyl lactates, d-limonene, pine oil, essential oils, sorbitol, 1,3-propane diol, tertiary alcohols of up to 8 carbon atoms, aromatic-substituted alcohols, polyalkylene glycols having up to 6 carbon atoms per alkylene group, mono- or dialkyl ethers of alkylene glycols or poly-alkylene glycols having up to 6 carbon atoms per glycol group and up to 6 carbon atoms in each alkyl group, mono- or diesters of alkylene glycols or polyalkylene glycols having up to 6 carbon atoms per glycol group and up to 6 carbon atoms in each ester group, combinations thereof and derivatives thereof.

51. A floor cleaning composition of claim 50, wherein the formulation can be concentrated to 32×, 64×, or 128×.

52. A biocidal composition, comprising:
about 0.1% to about 99.9% by weight of at least one surfactant having the following general Formula 1:

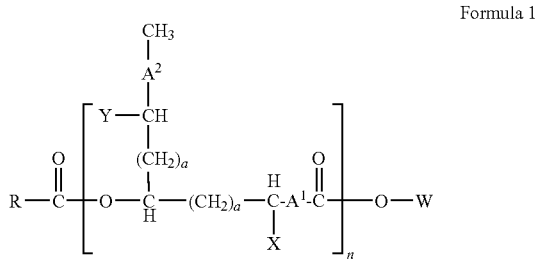

Formula 1 wherein n is an integer from 1-30, or mixtures thereof;
one of X and Y is $SO_3$—Z, the other of X and Y is H, and X and Y are independently assigned in each repeating unit;
$A^1$ and $A^2$ are linear or branched, saturated or unsaturated, substituted or unsubstituted, alkyl diradicals wherein the total number of carbons for each repeating unit is independent and in the range of $C_8$ to $C_{22}$;
a is 0, 1, or 2, and is independently assigned in each repeating unit;
R is linear or branched, saturated or unsaturated, substituted or unsubstituted hydrocarbon wherein the total number of carbon atoms is from 1 to 24;
W is H or a monovalent or divalent metal cation, ammonium cation, substituted ammonium cation, or an alkyl or substituted alkyl group; and
Z is H or a monovalent or divalent metal cation, ammonium or substituted ammonium cation;
about 0.001% to about 40% by weight of at least one biocidal agent; and
about 0.1% to about 99% of at least one carrier.

* * * * *